US005459536A

United States Patent [19]
Shalon et al.

[11] Patent Number: 5,459,536
[45] Date of Patent: Oct. 17, 1995

[54] APPARATUS AND METHOD FOR AUTOMATED PERIMETRY

[75] Inventors: Tadmor Shalon, Brentwood; Marvin L. Pund, Chesterfield; Susan L. Bragg, University City; Mark Szus, Olivette, all of Mo.

[73] Assignee: Alcon Laboratories, Inc., Fort Worth, Tex.

[21] Appl. No.: 174,181

[22] Filed: Dec. 27, 1993

[51] Int. Cl.⁶ .................................................. A61B 3/02
[52] U.S. Cl. ........................ 351/226; 351/222; 351/224
[58] Field of Search ................................. 351/226, 224, 351/222, 223, 225, 237

[56] References Cited

U.S. PATENT DOCUMENTS

| | | | |
|---|---|---|---|
| 3,515,466 | 6/1970 | Apple | 351/23 |
| 3,705,003 | 12/1972 | Lynn, Jr. et al. | 351/39 |
| 3,713,386 | 2/1973 | Lynn, Jr. et al. | 351/39 |
| 3,883,235 | 5/1975 | Lynn, Jr. et al. | 351/39 |
| 3,936,164 | 2/1976 | Cohen et al. | 351/23 |
| 3,984,156 | 10/1976 | Jernigan | 351/6 |
| 4,012,128 | 3/1977 | Regan | 351/17 |
| 4,045,130 | 8/1977 | Krahn | 351/24 |
| 4,059,348 | 11/1977 | Jernigan | 351/30 |
| 4,075,657 | 2/1978 | Weinblatt | 358/93 |
| 4,145,123 | 3/1979 | Krahn et al. | 351/24 |
| 4,260,227 | 4/1981 | Munnerlyn et al. | 351/24 |
| 4,346,968 | 8/1982 | Melin et al. | 351/23 |
| 4,429,961 | 2/1984 | Sheingorn | 351/226 |
| 4,561,738 | 12/1985 | Humphrey et al. | 351/226 |
| 4,675,736 | 6/1987 | Lehmer et al. | 358/183 |
| 4,712,894 | 12/1987 | Nunokawa | 351/208 |
| 4,712,895 | 12/1987 | Kamlyama et al. | 351/243 |
| 5,220,361 | 6/1993 | Lehmer et al. | 351/226 |

OTHER PUBLICATIONS

Kowa Company, Ltd., brochure AP–340 KOWA Automated Visual Field Plotter (8 pages) Feb. 1991.
Kowa Company, Ltd., brochure AP–125 KOWA Automated Visual Field Plotter (4 pages) Feb. 1991.
Interzeag OCTOPUS 1-2-3 Combination (diagnostic program) Dec. 1991 (2 pages).
Bio–Rad Ophthalmic Division, brochure Automated Perimetry System (2 pages) Oct. 1990.
Keeler Instruments Inc., brochure Henson CFA 3000 (6 pages) Dec. 1991.
Interzeag Medical Technology, brochure #5 Octopus 1–2–3 (6 pages) 1989.
David E. Silverstone, "Automated Visual Field Testing", Appleton–Century–Crofts, Norwalk, Conn. 1986, pp. 53–87.
Michael V. Drake, M.D., A.B., "The Visual Fields Text and Atlas of Clinical Perimetry".
The C. V. Mosby Company, St. Louis, Baltimore, Philadelphia, Toronto 1990, 4 pages.

Primary Examiner—William L. Sikes
Assistant Examiner—Hung Xuan Dang
Attorney, Agent, or Firm—Rogers, Howell & Haferkamp

[57] ABSTRACT

An apparatus and method for automated perimetry. A patient interface is adjustable with respect to a previously positioned patient rather than requiring the patient to position him or herself with regard to the perimeter. Fine adjustment of the patient interface with respect to the patient is possible while a perimeter dome is moved away from the patient and patient interface. Once positioned, the perimeter dome is moveable to a position adjacent the patient. A visual stimulus generating and directing device is preferably contained in a first module attachable to the dome. The visual stimuli are directed to various locations in the dome. An optional feature includes an eye sensing device which continuously monitors the size and position of a patient's pupil and correlates this information to the projected stimuli to verify the patient's fixation during testing. The eye sensor is preferably contained within a second module attachable to the dome. A connection device allows connection of either or both the projector and eye sensor to a stand alone processor. The device and method provide for industry standard tests and results, while being of a size which is portable and of a structural cooperation which does not require field servicing.

33 Claims, 14 Drawing Sheets

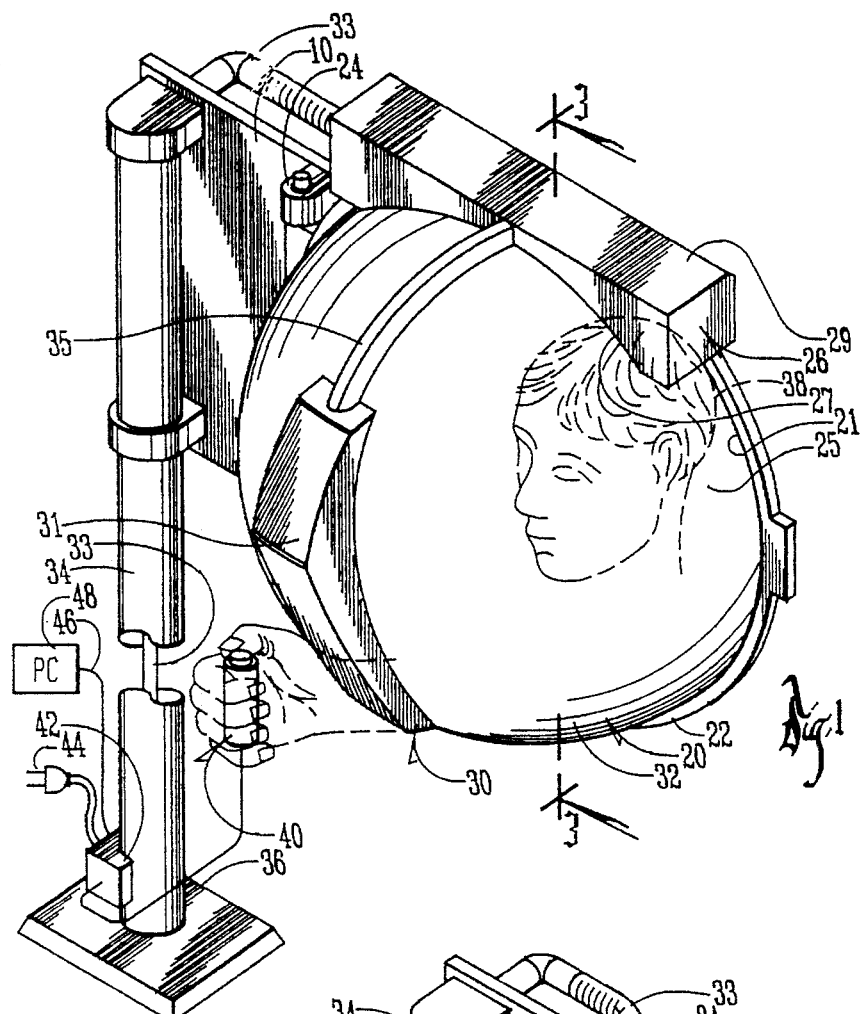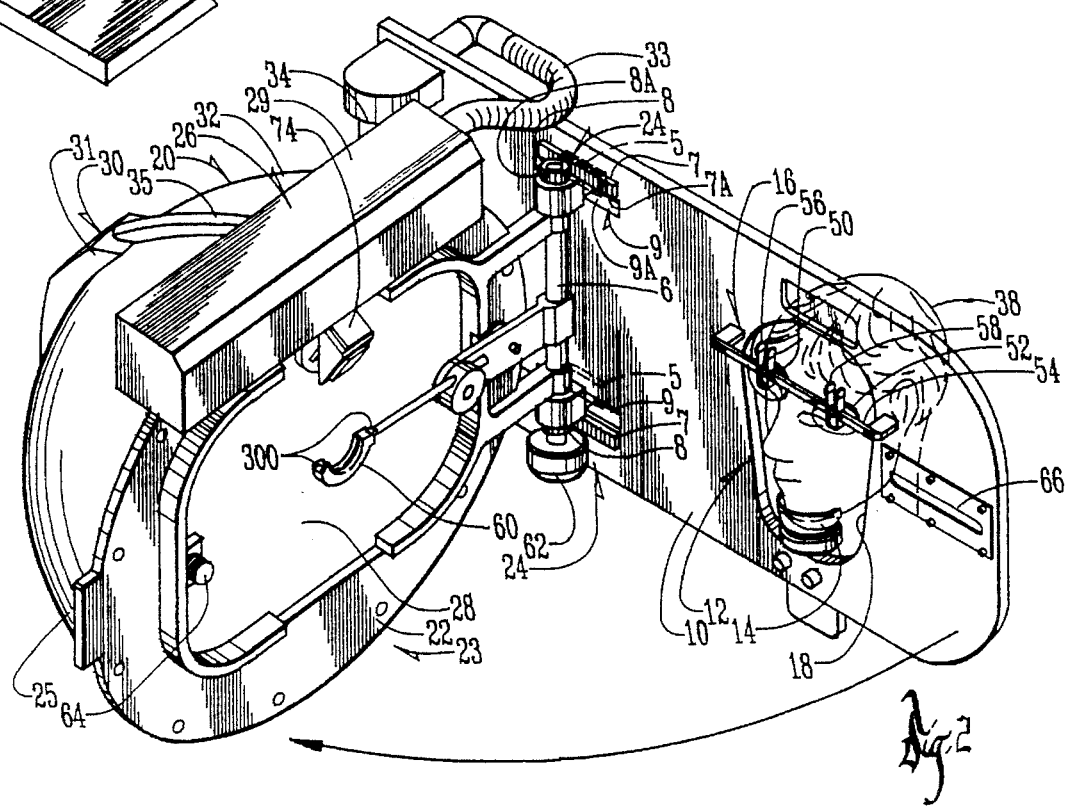

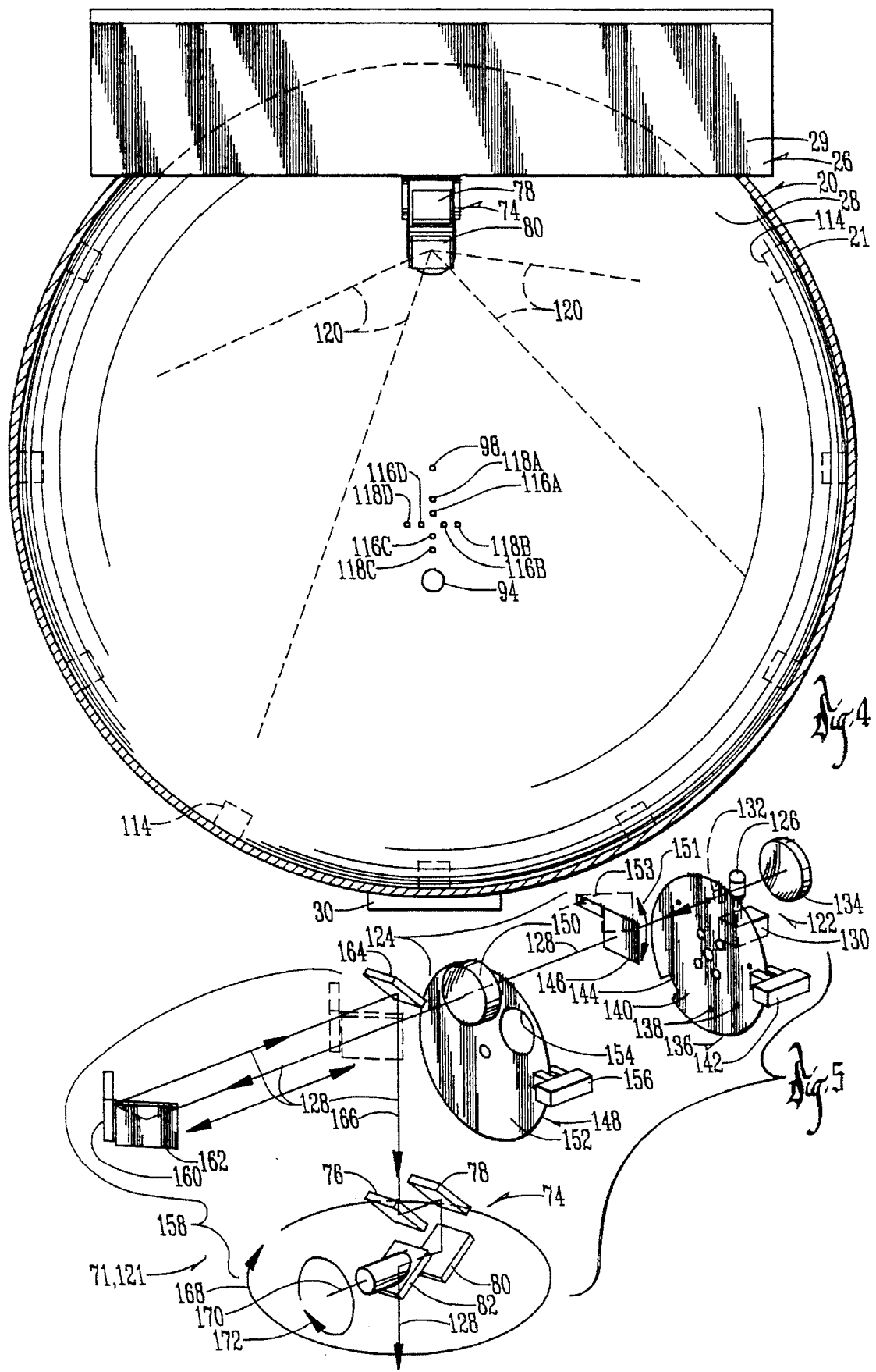

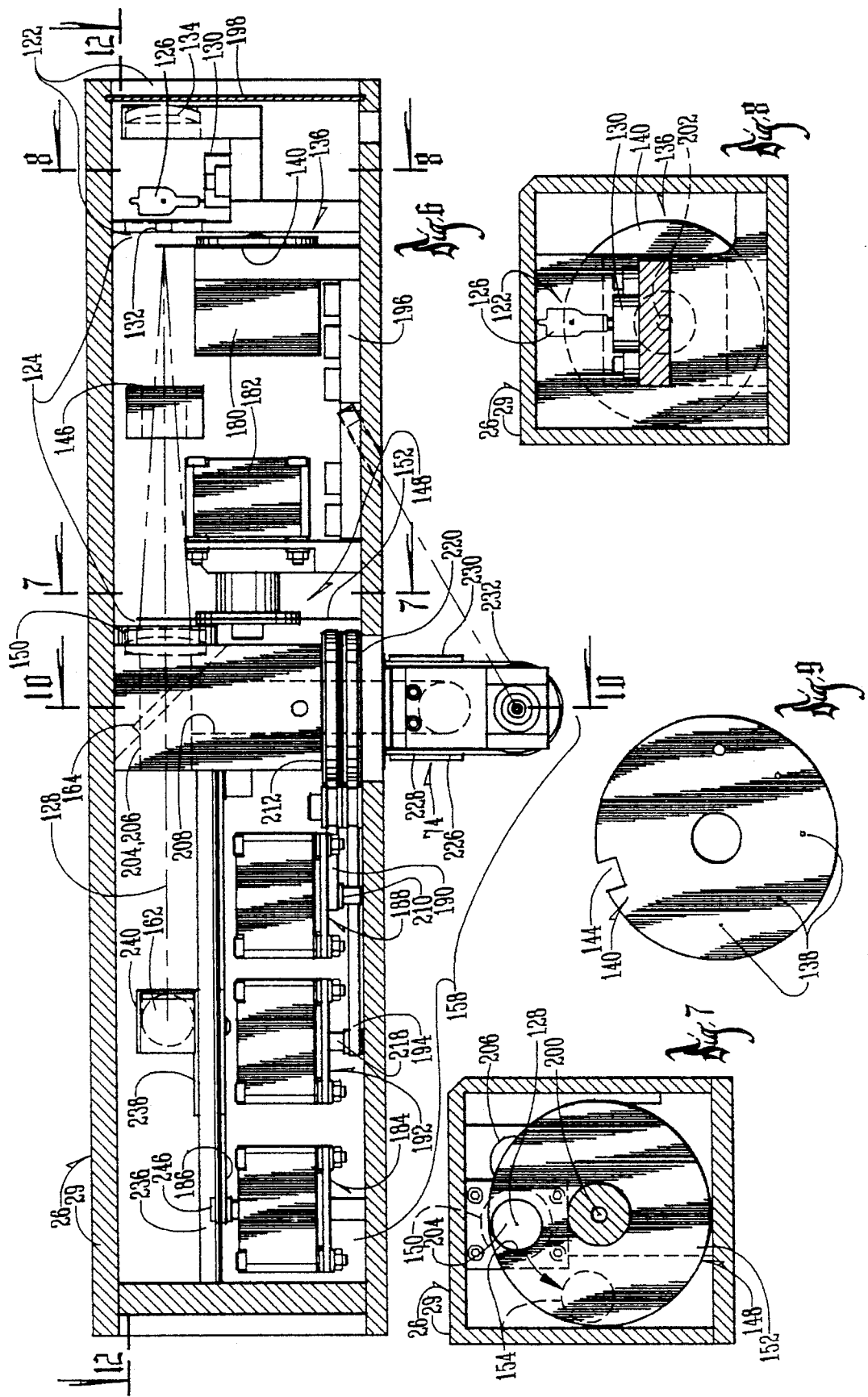

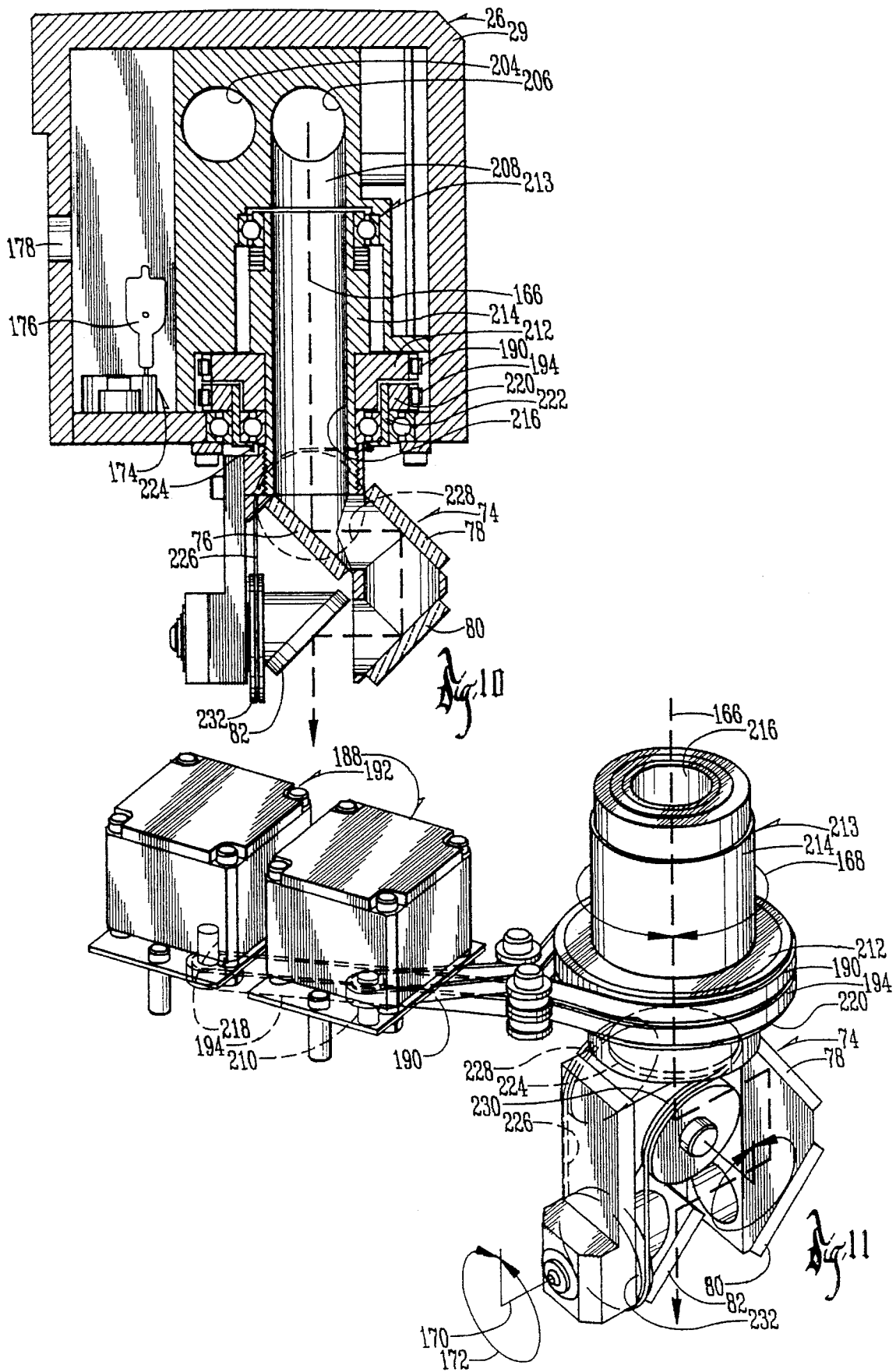

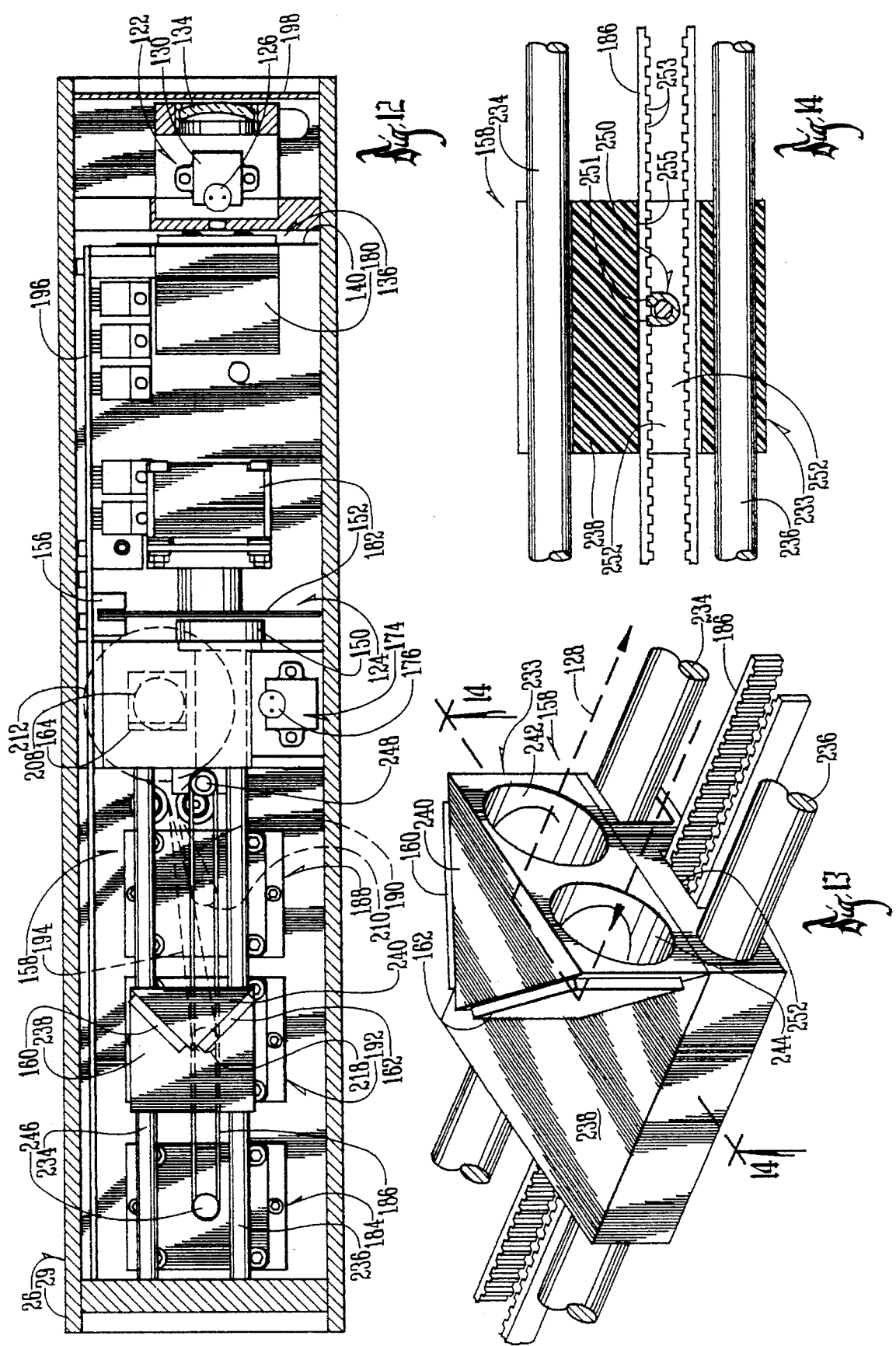

Fig. 22

APPARATUS AND METHOD FOR AUTOMATED PERIMETRY

BACKGROUND OF THE INVENTION

A. Field of the Invention

The present invention relates to perimetry, and in particular relates to an automated perimeter and a method of automated perimetry for perimetry-related tests and measures, including producing industry standard tests and results.

B. Problems in the Art

Perimetry is a well known area of visual testing. Perimetry generally involves measurements of retinal response relating primarily to the field of vision of a person. Such analysis by an eye care practitioner can be valuable in detecting and diagnosing major blindness-causing diseases, and can assist in treatment of such diseases. The basic concepts and procedures in perimetry testing have been long established and are well known in the art. See, for example, Drance, S. M. and Anderson, D. R. (Eds), *Automatic Perimetry in Glaucoma*, Grove and Stratton, Inc., Orlando, Fla. (1985); Silverstone, D. E. and Hirsch, J., *Automated Visual Field Testing: Techniques of Examination and Interpretation*, Appleton—Century-Crofts/Norwalk, Conn. (1986); Haley, M. J. (Ed), *The Field Analyzer Primer*, (2nd Ed.), Allergan Humphrey, San Leandro, Calif. (1987), which are incorporated by reference herein.

A conventional measurement procedure for perimetry is to have a patient fixate on a location and then signal when visual stimuli are perceived at various locations in the patient's field of view relative to that of the fixation point. If the patient does not perceive stimuli of certain intensities in certain locations, this indicates to the practitioner the possibility of vision-impairing problems.

Until relatively recently, manually operated perimeter instruments were utilized. See Anderson, D. R., *Perimetry With and Without Automation*, The C. V. Mosby Co., St. Louis, Mo. (1987), for a general discussion of manual perimetry. These instruments presented several difficulties. First, to obtain valid results, a well-trained, experienced technician or practitioner was needed. Furthermore, the testing procedure was usually long and exacting if accurate measures were to be taken. For example, visual stimuli to the patient had to be manually activated by the tester. Results had to be manually recorded by the tester or an assistant. A variety of systems have therefore been developed for automated, as opposed to manual, perimetry. Many of these are well documented and include several patents. See, e.g., Silverstone and Hirsh, supra, pages 53–81 and:

| U.S. Pat. No. | U.S. Pat. No. |
|---|---|
| 3,515,466 | 3,705,003 |
| 3,713,386 | 3,883,235 |
| 3,936,164 | 3,984,156 |
| 4,012,128 | 4,045,130 |
| 4,059,348 | 4,075,657 |
| 4,145,123 | 4,260,227 |
| 4,346,968 | 4,429,961 |
| 4,561,738 | 4,675,736 |
| 4,712,894 | 4,712,895 |

In essence, most automated perimeters attempt to allow the machine itself to adaptively (based on responses to previous stimuli) generate visual stimuli and record the patient's response to the stimuli as well as the parameters of the stimuli (e.g., exact location and intensity). This eliminates the manual record keeping and painstaking procedures of manual perimetry.

While many of the present day automated perimeters have advanced the art, problems and deficiencies still exist in this field, examples of which are discussed below.

Typical automated perimeters are large and relatively cumbersome. Size and weight of the machines have been driven somewhat by necessity. Most utilize a hemispherically shaped dome or a relatively large screen to create a defined and controlled viewing surface for the patient. In essence, this dome or screen requires a size larger than the patient's head to present a sufficiently large surface to test the field of view. It must be large enough, or adjustable, to allow both eyes to be measured. Additionally, the perimeter must accommodate both the patient and the operator from functional and comfort standpoints. The patient must be brought to the perimeter and have his/her head fixed and stabilized with respect to the perimeter to obtain accurate readings.

Additionally, the operator must have some way to not only operate the perimeter but to interact with the patient both physically (for head positioning) and verbally (for instructions).

Many present automated perimeters attempt to incorporate, in one device, all of the parts and components for a perimeter system. This would include a large housing containing the dome or screen, and structure to align and stabilize the patient's head, as well as optical, electrical, and electromechanical devices to generate visual stimuli and record the patient's responses in some fashion. Most automated perimeters, therefore, are of a size which makes them basically non-portable; the volume and weight essentially preventing one person from easily moving or transporting the perimeter from location to location within an office, or between buildings. Alternatively, present automated perimeters attempt to place most of the active components at various locations near or around the dome or screen. This results in rather large, bulky housings.

Other problems or deficiencies in the art include the fact that these rather large integrated units require field servicing and calibration. In other words, if some component, no matter how small or non-complex, fails, a service technician must travel to the device itself for servicing. These devices can not be easily taken or shipped to a central location. The practitioner or the office technician can not easily identify and isolate the failed component and replace it or ship it back to a central location for service.

Integrated, automated perimeters also tend to have deficiencies in the physical accommodation of the patient. In other words, these relatively large, non-portable devices require the patient to move up to the device rather than allowing the machine to be moved to the patient. Many times the final orientation of the patient is unnatural and uncomfortable. The perimetry tests, even with automated units, can take several tens of minutes, which makes this problem more acute. An uncomfortable position may be bearable for a few seconds or even minutes, but not for extended periods. It also may materially affect the test results.

Still further, size and configuration of many automated perimeters make it difficult for the practitioner or technician to interact with the patient. This can be particularly important with respect to verifying whether the patient is appropriately positioned to the perimeter and accurately reacting to the testing. For example, it is important to verify that the patient is fixating a known location during testing and that the patient's eye is open during presentation of each of the individual stimuli. Because the patient's head is basically stabilized in an opening to the dome in the relatively large housings of many current integrated perimeters (to allow view of the dome), such verification is difficult because the patient can not be easily viewed.

Some automated perimeters therefore have utilized verification systems which include such things as view holes through which the tester can watch the patient's eye through the housing and/or even video cameras that take a picture of the eye and present it on a monitor for the tester. Other attempts have been made but room for improvement still exists with respect to ease and accuracy of verifying the status of the patient's eye.

Some present automated perimeters do place some of the processing components outside the main perimeter housing or framework. However, these processing components are generally dedicated to the particular perimeter and are not "open" in the sense that they can be used with other types of perimeters.

A still further problem in the art relates to the value of being able to accomplish industry standard testing to obtain industry standard results. Certain automated perimeters which try to reduce the size of the device, or utilize different types of visual stimuli, may not be able to provide such testing and results.

OBJECTS AND ADVANTAGES OF THE INVENTION

It can therefore be seen that a need exists in the art for an improved automated perimeter and method of automated perimetry. Objects and advantages of the present invention therefore include:

1. Portability in the sense that the structure is relatively compact and light so that one person can move and transport components of the perimeter to various locations, rooms, or buildings.

2. Easy and comfortable positioning of the patient and tester, both during alignment and testing.

3. Easy and reliable quantitative verification of fixation of the patient before and during testing.

4. Easy and economical maintenance and servicing, and elimination of field calibration.

5. Flexibility and reliability for different patients, testing setups, operators, and locations.

All these objects and advantages apply while taking either static or kinetic perimetry tests and while producing industry standard testing and results. The nature of and importance of industry standard testing and results, and static and kinetic perimetry, are discussed for example, in Harrington, D. O. and Drake, M. V., *The Visual Fields: Test and Atlas of Clinical Perimetry*, (6th Ed.), The C. V. Mosby Co., St. Louis, Mo. (1990), incorporated by reference herein.

Perimetry tests can be administered by a trained eye care practitioner or technician. One of the advantages of the present invention is that the level of training required for accuracy of the perimetry measurements is reduced, thereby allowing technicians to perform the testing and the practitioner to interpret the results. Another advantage is that the amount of time required for the readings is reduced.

Perimetry procedures require concentration on the part of the patient and can require a significant amount of time. Anything that promotes patient comfort may improve the test results. One advantage of the apparatus of the present invention is the ability to position the patient comfortably in the instrument while the dome is open. The open dome/patient interface is easier for both the operator and the patient during alignment. It allows for greater accuracy in positioning and better patient comfort.

Another advantage of the present invention is a quantitative eye tracking system. The operator can not only accurately position the patient, but also validate patient data during testing.

Perimetry testing usually is performed at a designated, relatively permanent location in an eye care practitioner's office or a medical facility. One of the other advantages of the present invention is the portability of the invention to allow it to be moved from place to place within an office or building, or even easily transported to different locations to allow the testing equipment to be taken to locations other than specialized hospital departments or clinics; even to a patient's home or other current residential location.

These and other objects, features, and advantages of the present invention will become more apparent with reference to the accompanying specification and claims.

SUMMARY OF THE INVENTION

The present invention comprises an apparatus and method for automated perimetry.

The apparatus according the invention presents an integrated system that includes: A relatively portable and compact structure that in turn includes:

(a) a patient interface that allows placement of the perimeter to the patient instead of vice versa because of relatively small size, portability, and adjustability to the patient, and a swing-away or otherwise moveable dome to allow direct access to the patient when adjusting the perimeter in place;

(b) a smaller dome than conventionally utilized;

(c) modular active components such as a device for generating visual stimuli and a device for sensing the state of the patient's eye during testing so that servicing and maintenance of the perimeter can be accomplished by removing a modular component and sending it to a central servicing location instead of requiring on-site maintenance or servicing;

(d) components to automatically and quantitatively verify proper pupil fixation during the presentation of each and every stimulus;

(e) utilization of a connector to a stand-alone processor which controls the perimeter, removing a substantial amount of the processing, operator interface, and data collection tasks from the structure which is physically interfaced with the patient; and (f) processing software that coordinates operation for quick, highly accurate industry standard testing and results.

The method according to the present invention includes:

(a) perimetry testing by primarily adjusting the perimeter with respect to the patient and not vice versa;

(b) industry standard testing and results with a compact portable device;

(c) eye tracking for continuous validation of results;

(d) flexible and comprehensive processing and storage of testing information.

Other features, options, and advantages will be appreciated with reference to other portions of this specification.

BRIEF DESCRIPTION OF THE DRAWINGS

FIG. 1 is a partial perspective view, partial diagrammatic view of an apparatus according to the present invention, as brought into a position relative to a patient.

FIG. 2 is an isolated perspective view of the patient interface and dome of FIG. 1, with the dome swung away from the patient.

FIG. 4 is a slightly reduced in size sectional view taken along line 4—4 of FIG. 3.

FIG. 5 is a diagrammatic depiction of the interior optical components of the engine controller of the apparatus of the present invention.

FIG. 6 is an enlarged sectional view taken along line 6—6 of FIG. 3.

FIG. 7 is a sectional view taken along line 7—7 of FIG. 6.

FIG. 8 is a sectional view taken along line 8—8 of FIG. 7.

FIG. 9 is an enlarged isolated elevational view of an example of a pinhole wheel such as can be used in the configurations of FIG. 5 and 6.

FIG. 10 is an enlarged sectional view taken along line 10—10 of FIG. 6.

FIG. 11 is a still further enlarged isolated perspective view of portion of the projector of the engine controller of FIGS. 6 and 10 according to the apparatus of the present invention.

FIG. 12 is a sectional view taken along line 12—12 of FIG. 6.

FIG. 13 is an enlarged partial perspective view of a portion of other interior components of the engine controller of FIGS. 6 and 10, according to the apparatus of the present invention.

FIG. 14 is a sectional view taken along line 14—14 of FIG. 13.

FIGS. 21 and 22 are exemplary replications of PC screens used with the software of the apparatus of the present invention.

DETAILED DESCRIPTION OF THE INVENTION

A. Overview

Figure 3:
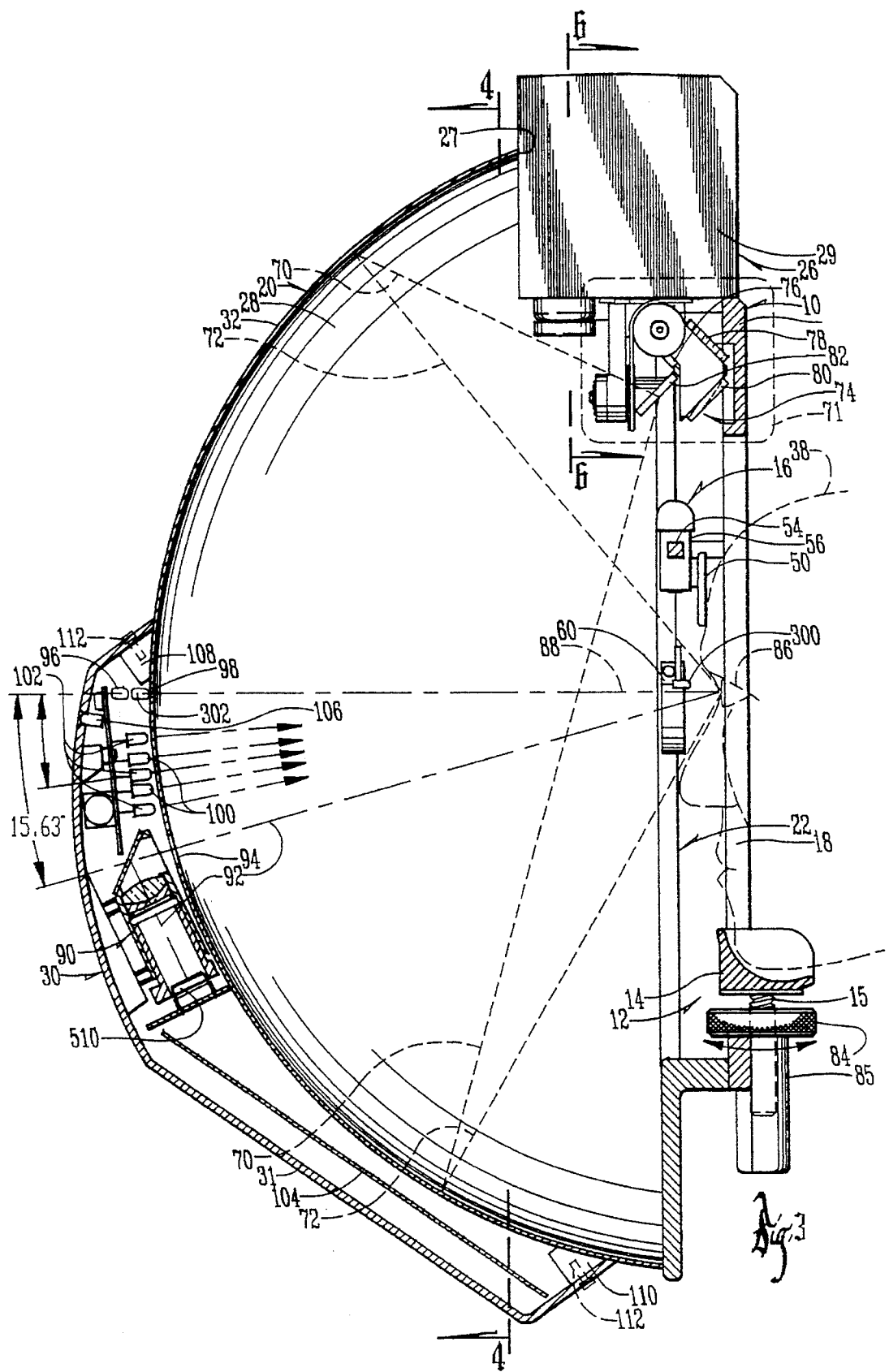
FIG. 3 is an enlarged sectional view taken along line 3—3 of FIG. 1.

To assist in a better understanding of the invention, the invention will now be described in detail. The preferred embodiment disclosed is set forth for purposes of example and not by way of specific limitation to the invention.

As previously mentioned, perimetry is a well known procedure in the art. As previously cited, a number of references discuss perimetry, as well as the current state of perimetry equipment. There are certain standards regarding perimetry that are also known or available to those skilled in the art. An example is *Perimetric Standards and Perimetric Glossary of the International Counsel of Ophthalmology*, 1979 edition J. M. Enoch, The Hague: W. Junk.

The following detailed description will refer frequently to the appended drawings. Reference numerals and letters will be utilized to indicate certain parts and locations in the drawings. The same reference numerals or letters will be used to indicate the same parts or locations throughout the drawings unless otherwise indicated.

B. General Discussion of The Invention—Perimetry

The apparatus is used to take perimetry readings from a patient. The patient's head is stabilized relative to the perimeter structure and a visual stimulus (in the form of a small spot of light) is randomly projected to different positions at different brightness levels, for a specified time duration, on the interior of a portion of the structure known as the dome or bowl.

The patient is requested to fixate on an indicated location (a fixation target) while the stimuli are displayed. If the patient perceives the presence of a stimulus against a controlled background level of light, he/she is instructed to push a manually operated patient switch. The procedure therefore attempts to map out the field of vision of the patient and detect any areas of that field of vision which may be less sensitive than other areas.

This testing is done one eye at a time. The validity of the test results depends upon the good faith responses of the patient, and further on whether the patient remains fixated on the fixation target and keeps his/her eye open during presentation of the various visual stimuli.

C. General Mechanical Structure of the Preferred Embodiment

FIGS. 1 and 2 illustrate what will be called the basic perimeter chassis or structure of the apparatus of the present invention. Face plate 10 (see also FIG. 2) includes patient interface (the area indicated generally at 12) consisting of chin rest 14 and forehead rest 16 to receive and stabilize a patient's head in opening 18 in face plate 10. Bowl or dome 20 having a hemispherical shape includes flange or dome frame (and mounting bracket) 22 attached around edge 21 of its open side 23. Dome 20 has a 23.9 centimeter (cm) radius. The size can vary, but the optical relationships then must be conformed to that size. Dome 20 is pivotable on sliding hinges 24 (connected to face plate 10) between a closed position against face plate 10 (see FIG. 1) and an opened position (see FIG. 2).

Two modular components are removably mounted to dome 20 on its back side 25. Engine controller 26 is set into and releasably secured to cutout portion 27 at the top of dome 20 (see also FIGS. 3 and 4). Engine controller 26 basically includes, in a single module or housing 29, all of the components required to generate and project the visual stimulus onto the interior surface 28 of dome 20, to control the ambient light level within dome 20, and to record the patient's response. Interior surface 28, in the apparatus, is designed to be a white Lambertian reflector, such as is known in the art.

Eye tracker 30 is mounted to the exterior 32 of dome 20, including a portion positioned approximately at the back apex of dome 20. Eye tracker 30 includes, in a single module or housing 31, the components to generate a fixation target for the patient as well as a system to monitor, on a continuous and quantitative basis, the fixation of the patient's eye during testing. The components, as well as the operation of engine controller 26 and eye tracker 30, will be specifically detailed later in this description.

As depicted in FIG. 1, face plate 10 can be secured to a vertical pole 34 that extends upwardly from base 36 (shown diagrammatically). Base 36 can either be an attachment to a wall, or a mobile structure (e.g. a wheeled cart) that sits on the floor, or a table surface. Pole 34 is adjustable in vertical height by means well within the skill of those skilled in the art to allow vertical positioning of face plate 10 and dome 20 with respect to patient 38 (usually seated). Adjustment can be assisted by, for example, a built-in gas spring (not shown).

FIG. 1 also illustrates patient switch 40; in this case, a hand-held push button (Radio Shack joy stick 270-1704, single pole, single throw momentary switch) that is electrically connected to circuitry (see FIG. 16) in engine controller 26 via its releasable connection to power supply/cable interface 42. Interface 42 houses the electrical power supply (not shown) for the apparatus and also is the beginning point of a wiring harness or cable system 33 that allows electrical communication to other components of the perimeter. Power supply/cable interface 42 is connectable by standard electrical plug 44 to any conventional household alternating current and transforms that current into electrical power usable by engine controller 26 and eye tracker 30. The power supply in interface 42 consists of U.S. ELCO K150 AU-24-N 24 Volt and U.S. ELCO K50 AU-5-N 5 Volt power supplies contained in a chassis (not shown) and connected to line AC via plug 44. The chassis also contains an on-off switch and a circuit breaker (not shown). The two power supplies output +19 D.C. volts and +6 D.C. volts respectively. Wiring harness 33 can be built into pole 34 to distribute the power to the engine controller 26 and eye tracker 30.

It is to be understood that a standard, known-in-the-art RS232 connector (reference number 46—see FIG. 15 for specific connections) is electrically connected to engine controller 26 and eye tracker 30 using wiring harness 33 and allows releasable connection to a stand-alone processor 48 (in the apparatus a personal computer or PC).

It can therefore be seen that the apparatus is of a relatively compact size, and easily moveable and adjustable so that it can be brought and adjusted to the patient 38 (instead of adjusting the patient to the machine). Two modules (engine controller 26 and eye tracker 30) contain the major active components and electrical circuitry for the perimeter. Additionally, the RS232 connector 46 allows the apparatus to be quickly and easily connected to a stand-alone and separate processor 48, eliminating that space-consuming equipment from the physical chassis or housing related to the patient interface 12 and dome 20.

By referring to FIG. 2, additional details regarding the physical structure of the apparatus can be seen. Head of patient 38 is shown in testing position in patient interface 12. Chin rest 14 is vertically adjustable to center the specific eye of patient 38 to be tested relative to lens holder 60 when moved to opening 18. Forehead rest 16 has first and second pads 50 and 52 which can be horizontally adjusted by sliding along bar 54 with brackets 56 and 58 to fit various patient heads, postures and positions, and to limit motion of the patient's head during testing.

Face plate 10 can be pivoted around pole 34 to bring patient interface 12 to patient 38. The selected eye is centered by moving dome 20 on sliding hinges 24 while the patient's head is stabilized in opening 18. This is distinctly different from most conventional automated perimeters which require the patient to move to and then adjust to the position of the machine.

FIG. 2 also shows that a trial lens holder 60 can extend from shaft 6 (extending between sliding hinges 24) to opening 18. The purpose and use of trial lenses (not shown) is well known in the art. Lens holder 60 can hold up to three lens and is adjustable toward and away from the patient's face and serves to provide a receptacle to hold at least one lens in the line of sight of the patient's eye being tested. It may be pivoted upward to remove it from the patient's field of view. It moves, however, with dome 20 rather than face plate 10, and once in place is always aligned with the center of dome 20.

Sliding hinges 24 serve several functions. First, they allow dome 20 to swing away from face plate 10 to allow the operator of the perimeter direct access to the patient's head on either side of face plate 10 or through opening 18 to easily adjust the perimeter to the patient, and also operate the fine adjustments of the chin and forehead rests, as well as adjust lens holder 60. The sliding hinges 24 also allow either eye to be centered and measured. Each sliding hinge 24 is slideably mounted in top and bottom horizontal slots 9 extending through the thickness of face plate 10, slots 9 extend through the entire thickness of face plate 10. Associated horizontal racks 7 parallel the slots 9 and, have vertically aligned, spaced apart teeth 7A. The top rack 7 is just above its associated slot 9. The bottom rack 7 is just below its associated slot 9 (see FIG. 2). Pinion gears 8 are mounted near opposite ends of shaft 6 and have teeth 8A which mesh with all associated rack 7. By rotating control knob 62, the entire dome 20 can be adjusted horizontally. Retaining brackets 5 are connected to sliding hinges 24 on the side of face plate 10 opposite from racks 7 and pinion gears 8 by screws, bolts, or other structures or ways. Brackets 5 are larger in height than slots 9 thus retaining hinges 24 to face plate 10 (and holding pinion gears 8 meshed to racks 7), but allow slideable movement of hinges 24 along slots 9. Hinges 24 support the weight of dome 20 along the lower surfaces 9A of slots 9. A friction-reducing component (such as a Teflon sheet) could be placed on surfaces 9A. Dome 20 can be releasably secured to face plate 10 in a closed position by virtue of magnetic latch 64 and receiver 66. Other connection means are possible.

Although a subtle concept, better patient comfort generally translates into higher quality test results, less testing time, and increased customer (patient) satisfaction.

D. Optical Components

1. Generally

FIGS. 3–14 set forth in more detail specifics regarding the structure of the apparatus, as well as its operation.

FIG. 3 is an enlarged sectional side elevational view of the apparatus with the patient 38 in position for testing. FIG. 3 shows how engine controller 26 is mounted in a cutout portion at the top of dome 20 and includes a projection system 71 (described in detail below) for projecting a spot of light to any position across a substantial portion of the interior surface 28 of dome 20 (see representative dashed lines 70 showing exemplary projections to top and bottom vertical positions of dome 20 respectively).

Two axis gimbal system (designated generally at 74) extends out the bottom of engine controller 26 and includes mirrors 76, 78, 80, and 82. As will be described in more detail later, these mirrors control an optical path for a projected light beam. A first rotational axis (see reference no. 166 in FIG. 5) for two axis gimbal system 74 provides azimuth pointing of the beam relative to dome 20, and a second axis (reference no. 170 in FIG. 5), provides elevational pointing of the beam relative to dome 20; so that coordinated together, the beam can be directed to all points on the interior surface 28 of dome 20, except those close to flange 22. Dashed lines 70 give an indication of the limit of the projected beam relative to the open face 23 of bowl 20 connected to flange 22. These boundaries, in association with the size of dome 20 and position of patient head 38, are sufficient to provide adequate field of view testing, indicated by dashed lines 72. As will be described additionally later, the beam is shuttered to produce limited duration "spots" in dome 20.

FIG. 3 shows that rotatable thumb wheel 84 can be used to vertically adjust chin rest 14 which is mounted atop a threaded rod 15. Rod 15 extends through a threaded aperture (not shown) in thumb wheel 84 down into hollow mounting housing 85, upon which wheel 84 is rotably attached. The patient's eye 86 can therefore be vertically positioned to align with axis 88 so that each patient has a uniform and consistent vision axis relative to the interior surface 28 of dome 20 where visual stimuli (spots produced by the light beam) can appear.

FIG. 3 also illustrates some of the interior components of eye tracker 30. What is essentially a camera 90 (solid state CCD imager system 90) is positioned within eye tracker housing 31 and has an optical axis 92 which captures an image through a relatively small opening 94 in the back of dome 20. Opening 94 is positioned on axis 92 which is several degrees (15.63° in the presently described apparatus) below axis 88 and is intended to allow CCD imager 90 to obtain an image of patient's eye 86. Eye tracker 30 captures images of the patient's pupil and sends data regarding the pupil's size and location to PC 48 continuously in real time during testing. This is quantitative information that is used to verify fixation during testing.

Eye tracker 30 also includes a bright red fixation LED 96 which is aligned along axis 88 and bright enough to illuminate a small opening 98 in dome 20. The patient is instructed to look and focus upon fixation LED 96. An infrared (IR) LED 302 is also positioned along axis 88 essentially right in front of LED 96. It functions to provide infrared illumination for eye tracker 30 when lens holder 60 is not used (lens holder 60 has its own IR LED(s) for this illumination purpose). LED 96 basically shines through IR LED 302 so that both can perform their function alone or simultaneously. The casing of LED 302 is basically transparent to facilitate this arrangement.

Eye tracker 30 also includes two sets of LED's 100 and 102 which are positioned, relative to eye 86, several degrees below fixation LED 96 and axis 88 but above opening 94 or axis 92. These LED's will be explained in more detail later. As shown in FIG. 3, eye tracker 30 also includes a printed circuit board 104 which contains all the electronics utilized for eye tracker 30, which will also be described in more detail later. In the apparatus, eye tracker housing 31 is shaped to closely conform to the exterior shape of dome 20. Anchors 108 and 110 are fixed to the exterior surface 32 of dome 20 by methods within the skill of those skilled in the art (for example, bolts, adhesives, rivets) and have threaded apertures to receive bolts 112 to bolt housing 31 and its interior contents to dome 20. Eye tracker 30 can therefore be easily removed from dome 20 for servicing or maintenance. Engine controller 26 is similarly removable.

Visible LED 106 is used to indicate to the operator that electrical power to the apparatus is on and also can be used to indicate status. For example, LED 106 can blink if the apparatus is operating correctly; but stay lit continuously if some malfunction occurs.

The distance between the bottom of engine controller 26 and optical axis 88 is approximately 6.5 inches. The front to back width of housing 29 of engine controller 26 is approximately 2.19 inches. The top to bottom length of housing 31 of eye tracker 30 is approximately 12.75 inches. Other dimensions can be used.

FIG. 4 illustrates a front elevational view of dome 20 without flange 22. It is to be understood that flange 22 (see FIGS. 2 and 3) can be connected to dome 20 by utilizing bonding clips 114 (two are labeled in FIG. 4 for purposes of example—but as shown, a plurality of these clips would be spaced apart around the entire opening of dome 20). Flange 22 could be attached to clips 114 by bolts or other methods within the skill of those skilled in the art.

FIG. 4 also shows in more detail the range of gimbal system 74 regarding placement of the light beam on the interior surface 28 of dome 20 (see dashed lines 120 which illustrate by example some of the locations on dome 20 to which a light spot stimulus could be diverted).

FIG. 4 also shows opening 98 for co-linearly mounted fixation LED 96 and infrared (or IR) LED 302 (Siemens SFH487-3), opening 94 for CCD imager system 90, and openings 116A–D and 118A–D for LED's 100 and 102 respectively.

LED's 100 (yellow) correspond to openings 116A–D, and LED's 102 (red) correspond with openings 118A–D. Therefore, essentially two diamond shapes, one inside the other, are presented. These LED's are utilized as alternate fixation targets. If, for example, a patient has macular disease or other central scotoma (which degrades central vision), which may not allow quality fixation on central fixation LED 96 along axis 88, either pattern of holes 116 A–D (inner small diamond) or 118 A–D (outer large diamond) can be utilized. The patient is instructed to fixate on the center of the smallest diamond which allows the patient to maintain steady fixation. The diamond patterns can also be used in such things as foveae testing, or otherwise. IR LED 302 in opening 98 is turned on only when the trial lens holder 60 (see FIG. 2) is not in use, and is used to illuminate the pupil for the eye tracker 30 CCD image.

2. Projection System

FIG. 5 depicts functionally how the projection system 71 of engine controller 26 works. FIG. 5 is not to scale and does not indicate precise positioning of the components relative to one another. A projector subassembly 121 inside housing 29 consists of an incandescent lamp/condenser optical system (shown generally at 122) and a projection optical system (shown generally at 124). System 122 produces an image of the incandescent tungsten filament of halogen lamp 126 (Gilway halogen L7404 technical lamp) along optical axis 128 for presentation to projection optical system 124. Lamp 126 is connected through base 130 (Gilway technical lamp base H992) to engine controller 26. As will be discussed further below, the electronics of engine controller 26 maintain or vary the brightness level of lamp 126. Biconvex condenser lens 132 (Melles Griot, Inc. 01 LDX 001 7 mm focal length (or f.l.), 5 mm diameter (or dia.)) condenses light received from lamp 126. Concave first surface mirror 134 (Edmund Scientific Co., 43,376, 13 mm f.l., 23 mm dia.) forms an image of the filament of lamp 126 superimposed onto the actual filament of lamp 126 to cause certain rays of light which form the filament image to pass through spaces in the actual filament and onto condenser lens 132 to increase the light through projection system 124.

Projection optical system 124 includes a pin hole wheel assembly 136 (VACCO PE-19 pinhole apertures in a 40 mm diameter pinhole disc) which follows condenser lens 132 and includes a selection of varying-in-size pin holes 138 (in this case six holes 138) arranged in an annular pattern around wheel 140. Optointerrupter 142 (using IR transmit and detect electronics) is positioned to receive the outer edge of wheel 140 (which includes a notch 144). Passage of notch 144 through optointerrupter 142 allows the system to know the exact rotational position of wheel 140 and consequently the position of the various pin holes which are placed to allow any of them to be aligned along optical axis 128. Rotation of a certain sized pin hole to optical axis 128 therefore allows the diameter of the light beam passed along axis 128 and therefore the size of the stimulus spot to be selected.

Projection system 124 also consists of a shutter 146, a neutral density filter wheel assembly(or NDF) 148, and a projection lens 150 (Edmund Scientific 32,327 achromatic lens, 100 mm f.l.). Shutter 146, such as is appreciated by those skilled in the art, consists of a motor driven occluder that upon instruction from the engine controller, either passes or blocks the light beam from lamp 126 to projection lens 150. It can take the form shown in FIG. 5 (basically a flag-shaped member rotated up and down (see arrow 151) about axis 153 by motor 412 (see FIG. 15)), but can take on other forms and configurations. Neutral density filter wheel assembly 148 includes film wheel 152 (photo process by Applied Image, Inc.) containing a variable neutral density filtering pattern around its circumference in addition to an opening 154 towards the outer perimeter of wheel 152, which functions both to provide a setting where no light from condenser lens 132 and shutter 146 is attenuated as it passes from a selected pin hole 138 to projection lens 150, and as a place that can be sensed by an optointerrupter 156 (as for optointerrupter 142) to assist in determining rotational position of wheel 152. As wheel 152 is rotated from opening 154, the wheel changes from being almost transparent to being opaque. This allows the brightness of the filament image of lamp 126 to be varied. NDF wheel 152 is positioned near the projection lens 150 aperture stop so that the variation in optical density across the optical path will not cause a variation in the intensity of the final pin hole image projected on to the interior surface 28 of dome 20.

Projector lens 150 forms an image of the selected pin hole 138 from pin hole wheel 140 at a fixed distance (approximately 22 inches) in front of projector lens 150. A constant projection distance is used because it produces an image of constant brightness and size through a series of seven flat first surface mirrors (23 mm×17 mm×3.2 mm, Denton Vacuum Co. FSS-99 coating) comprising a beam steering and focusing mirror system (indicated generally at 158).

System 158 includes mirrors 160 and 162 that, as shown in FIG. 5, are moveable as a unit along optical axis 128. Mirrors 160 and 162 function to redirect the beam path by 180°. Their movement along optical axis 128 maintains a constant total path length from projection lens 150 to any chosen point on interior surface 28 of dome 20. Fixed mirror 164 directs the optical path coincident to the azimuth rotation axis 166 relative to gimbal system 74.

Mirrors 76, 78, 80, and 82 of gimbal system 74 (as previously discussed with regards to FIG. 3) are as a group (as shown by arrow 168) rotated around azimuth rotation axis 166 to provide azimuth pointing of the projected beam relative to the dome and to direct the optical path to be coincident to elevation axis 170. As shown by arrow 172, mirror 82 is rotatable around elevation axis 170 to provide elevation pointing of the projected spot relative to dome 20.

3. Background Illumination

Other optical components of the apparatus include a lamp assembly 174 (see FIG. 10) used to provide uniform background illumination across the interior surface 28 of dome 20 viewed by the patient. Lamp assembly 174 includes lamp 176 (Gilway L7404 and base H992) enclosed in housing 29 for engine controller 26. Light from lamp 176 is directed out opening 178 in housing 29 positioned to direct light onto an area of interior surface 28 of dome 20 not visible to the patient. Interior surface 28 has a Lambertian reflection characteristic so that reflected light from the illuminated area produces a uniform brightness across the interior surface 28 visible to the patient.

The optical characteristics of the eye tracker 30 will be explained in detail later. Engine controller 26 includes all of the optics for generating and directing a light spot, variable ill brightness, position, and diameter, to the interior dome surface 28. Any malfunction of any subcomponent of engine controller 26 can be serviced by quickly removing the entire engine controller 26, and sending it to a central servicing location. Immediately, the central servicing location can send a loaner engine controller 26 to the user of the perimeter. This can eliminate the requirement of on-site service calls and minimizes down time for the perimeter instrument.

4. Engine Controller Specifics

FIGS. 6–14 reveal in still further detail the structure of engine controller 26 of the apparatus. FIG. 6 shows the position inside housing 29, and structure of, lamp 126, mirror 134, condenser 132, pin hole wheel 140, neutral density filter wheel 152, projection lens 150, and mirrors 164 and 162. FIG. 6 also shows gimbal system 74 extending from housing 29.

FIG. 6 additionally shows several stepper motors which drive several of the above mentioned components. They can be 16PY-Q203-01 stepper motors available from Minebea Co., Ltd. of Japan. Motor 180 turns pin hole wheel 140, and motor 182 turns neutral density filter wheel 152. Motor 184 operates belt 186 which moves the combined assembly (triangular housing 240, see FIG. 13) holding mirrors 160 and 162. Motor 188 moves belt 190 which rotates gimbal system 74, and motor 192 moves belt 194 which rotates elevation mirror 82 (not shown in FIG. 6; see FIGS. 10 and 11).

FIG. 6 also shows printed circuit board 196 holding circuitry, which will be explained further below, and that the housing 29 for engine controller 26 includes a removable end wall 198 for easy access to lamp 126.

FIG. 7 shows the position of neutral density filter wheel 152 with respect to the optical axis 128 for the light beam. In FIG. 7, opening 154 is positioned centered on axis 128. Motor 182 would turn axle 200 to rotate filter 152. For example, rotation of wheel 152 approximately 90° would move opening 154 to the position shown in ghost lines. The light beam along axis 128 would then pass through a portion of wheel 152 of a certain neutral density.

FIG. 8 shows the position of lamp 126 and how it can easily be accessed for replacement through removable end wall 198 (not shown). Pin hole wheel 140 is shown partially in ghost lines, as is axle 202 which would be connected to motor 180.

FIG. 9 shows an apparatus for pin hole wheel 140 including a variety of different sized pin holes 138. In the apparatus wheel 140 is a 40 mm metal (stainless steel) pinhole disc. It has an array of six pinholes 138 all with centers along optical axis 128 when rotated into position. The apparatus pinholes have diameters of 0.045, 0.720, 0,360, 0,180, 1,440, and 0.090 mm.

FIG. 10, as previously explained, shows the position of background illumination lamp 176. FIGS. 6 and 10 also show interior pathways 204, 206, and 208. The light beam from projector lens 150 travels through pathway 204 to mirror 162, then from mirror 160 back through pathway 206 to mirror 164, and then downwardly through pathway 208 to gimbal system 74.

FIGS. 10 and 11 in combination show in more detail how two axis gimbal system 74 is operated. Motor 188 operates a drive axle 210 which causes rotation of belt 190 around gear 212 of turret assembly 213. Gear 212 is connected to support sleeve 214 and extended tubular portion 216 (see FIG. 10) that extends down to gimbal system 74. Rotation of gear 212 therefore causes concurrent rotation of sleeve 214 and tubular extension 216, in turn causing like rotation of the entire gimbal system 74 around azimuthal axis 166.

In comparison, motor 192 operates rotation of drive axle 218 to move belt 194 around a gear 220. By referring also to FIG. 10, it can be seen that gear 220 is rotatably connected to a downwardly extending sleeve 222 which ends with a flange 224 that receives a portion of thin drive belt 226. By referring to both FIGS. 10 and 11, a combination of pulleys 228, 230, and 232 (and associated belt 226) cooperate with flange 224 to direct drive power to rotate mirror 82 around elevational axis 170. Thus, the entire gimbal system 74 can rotate around axis 166, and mirror 82 on gimbal system 74 can be independently rotated around axis 170.

FIGS. 12–14 show in more detail the structure that allows movement of mirrors 160 and 162. As previously explained, this combination of mirrors functions to redirect the light beam path 180° and maintain the spot focus on dome 20. This is accomplished in the apparatus by trombone slide system 233. Two parallel rods 234 and 236 are secured in engine controller 26 as shown in FIG. 12. A carriage 238 slides along rods 234 and 236. Triangular housing 240 holds mirrors 160 and 162 and includes openings 242 and 244 to allow entry and exit of the light beam. Openings 242 and 244 coincide with pathways 204 and 206 shown in FIG. 10.

Precise movement of carriage 238 along rods 234 and 236 is provided by operation of motor 184 which rotates drive axle 246 which in turn moves notched belt 186 which is held in tension around drive axle 246 and pulley 248 (see FIG. 12).

As shown in FIG. 14, belt 186 is secured to carriage 238 by a clamp member 250 that has mating portions 251 that extend into notches 253 in notched belt 186 aligned with portions 251 and clamp it against a surface 255 of channel 252 in the bottom of carriage 238. Movement of belt 186 therefore causes concurrent linear movement of carriage 238 along rods 234 and 236.

The basic structure of the apparatus has been described. It is to be understood that the specific structure is but one example of structure that can perform the various functions of the invention.

E. General Electrical/Mechanical Layout

Figure 15:
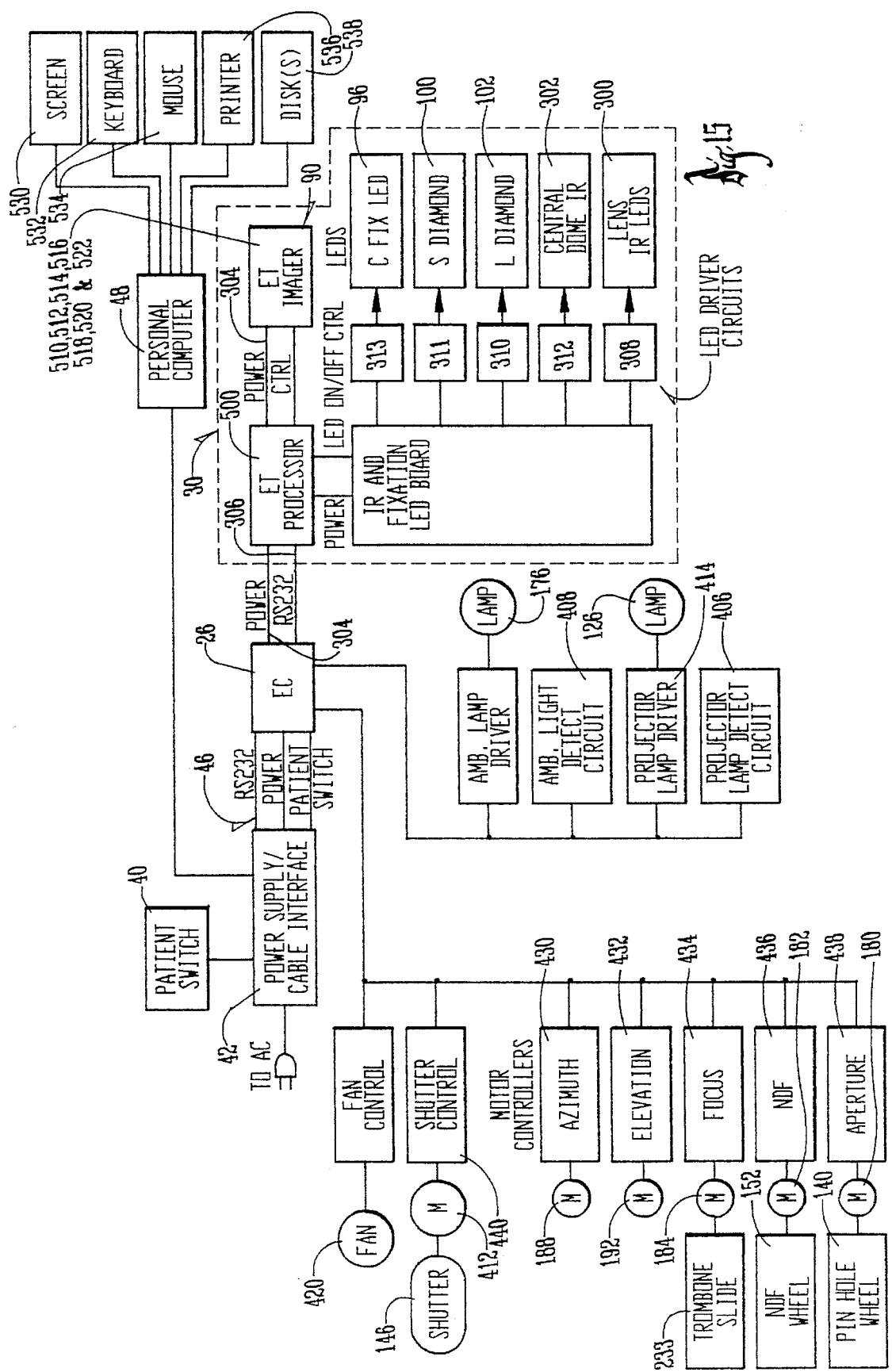
FIG. 15 is a block diagram of the hardware and electrical interconnection between components of the apparatus of the present invention.

FIG. 15 illustrates in block form the electrical interconnection of components in the apparatus. As previously stated, personal computer 48 is connected via a standard RS232 serial communication link 46 to the remainder of the perimeter system. PC 48 plugs into power supply/cable interface 42, and is thus connected to wiring harness 33 which includes RS232 communications link 46. Engine controller 26 is the central component for the apparatus. Patient switch 40 is connected to engine controller 26 via power supply/cable interface 42 and wiring harness 33. In the apparatus, one or more (preferably two) infrared (IR) LED's 300 (see FIG. 3) can be positioned on lens holder 60 to direct infrared light on the patient's pupil when the trial lens holder 60 is used. IR LED's 300 are connected to eye tracker 30 and are turned on or off by an LED on/off control 308 (transistor switch 2N3904) activated by computer 48. Alternatively, when holder 60 is not used, dome IR LED 302 (with computer LED on/off control 312)(see FIG. 3) is used to illuminate the patient's eye for eye tracker 30. Eye tracker 30 also includes fixation LED's 96, 100 and 102 (with computer LED on/off controls 313, 311 and 310).

FIG. 15 shows how electrical power is supplied to the system and how data communication occurs between engine controller 26, eye tracker 30, and personal computer 48. The power supplies in power supply/cable interface 42 convert household AC into DC power and send it to engine controller 26. Power cable 304 then provides DC power to eye tracker 30 by connection between engine controller 26 and eye tracker 30.

Similarly, RS232 pass-through cable 306 is connected between engine controller 26 and eye tracker 30. By standard, known-in-the art components in engine controller 26, communication over serial communication link 46 is possible. At any one time, the personal computer 48 selects information going between eye tracker 30 and personal computer 48 or information going between engine controller 26 and personal computer 48.

This arrangement therefore allows a minimum number of connections and simplifies the assembly and disconnection of components.

F. Engine Controller Electronics

Figure 16:
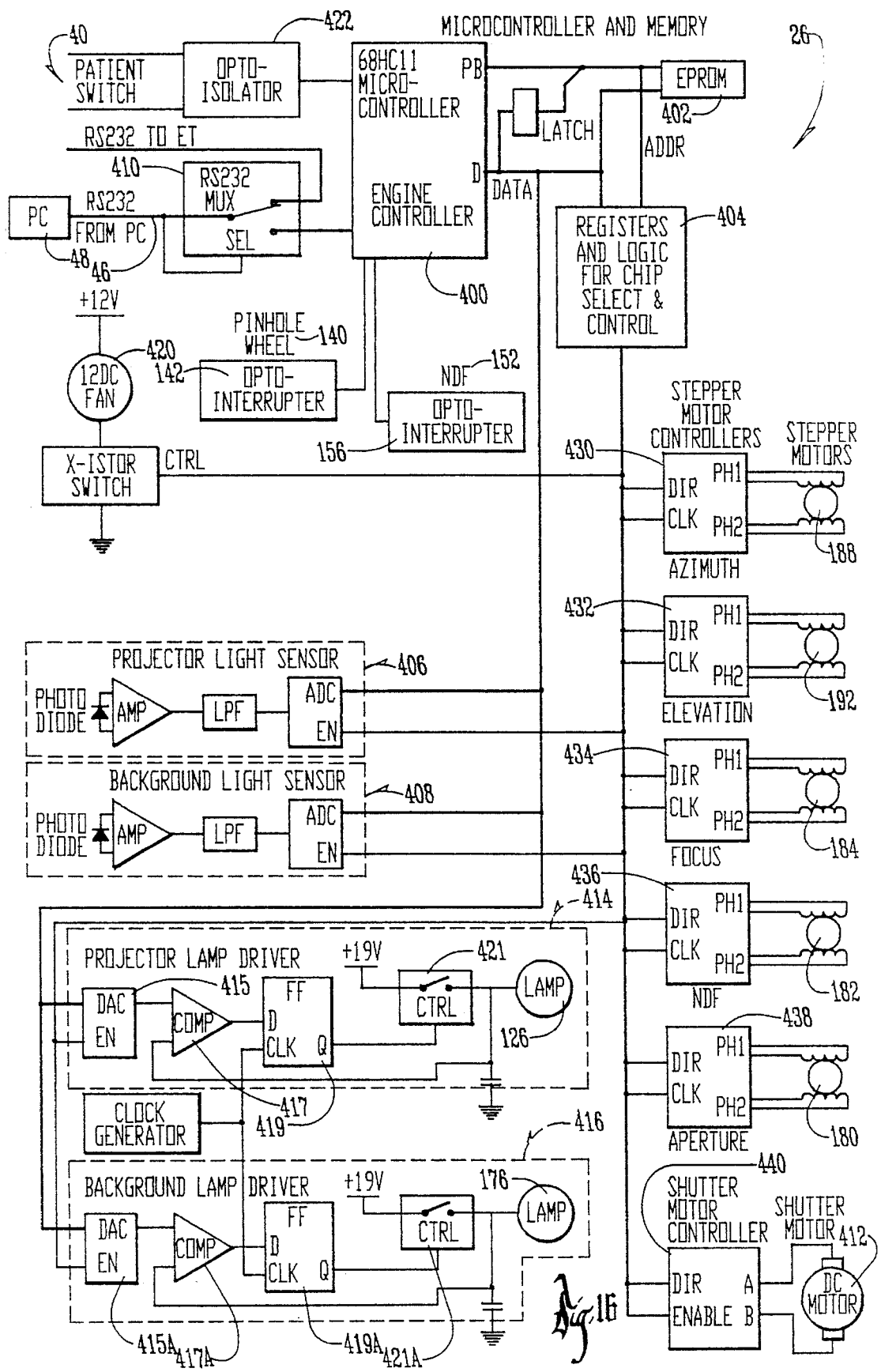
FIG. 16 is a more detailed block diagram of the engine controller (EC) of FIG. 15 according to the apparatus of the present invention.

FIG. 16 provides a block diagram of the specific contents of engine controller 26 according to the apparatus of the present invention. A microcontroller 400 cooperates with EPROM 402 and registers 404 to perform a variety of functions for engine controller 26.

The engine controller 26 is a microcontroller based design. Microcontroller 400 (TOSHIBA TMP68HC11E1T) is a 68HC11E2 8-bit microcontroller with several built-in peripherals, including RAM, EEPROM, a multiplexed analog to digital converter or ADC, synchronous and asynchronous communications ports, timers, and several general purpose, registered, programmable I/O lines. The 32K external EPROM 402 (Advanced Micro Devices AM27C256-175) holds microcontroller 400's firmware. Several IC's create the chip select and static control lines required by the microcontroller to control the external peripherals.

First of all, microcontroller 400 receives information from (a) patient switch 40 (through optoisolator 422) regarding whether the patient indicates a spot is observed or not, (b) optointerrupters 142 and 156 regarding the rotational position of pinhole wheel 140 and NDF wheel 152, and (c) projector light and background light sensors 406 and 408 (EG & G. VACTEC VTB1013B photo diodes and associated analog amplifier circuitry, low pass filters, and analog to digital converters) regarding the intensity of lamps 126 and 176; thus monitoring their status. Additionally, multiplexor switch 410 (Texas Instruments SN74HC157N) is controlled by PC 48 to select whether communication from PC 48 is to engine controller 26 or eye tracker 30 along serial link 46. This therefore comprises the RS232 pass-through ability of the apparatus.

Microcontroller 400 also operates the following components of engine controller 26. The stepper motors 180, 182, 184, 188, and 192 control size, brightness, focus and position of the stimulus spot when driven by associated stepper motor controllers 438, 436, 434, 430, and 432 respectively (Motorola SAA1042). Shutter motor 412 (a DC servo motor), controlled by a shutter motor controller 440, operates shutter 146 to select spot duration. As shown in FIG. 16, microcontroller 400 operates projector lamp driver 414 which includes a digital to analog converter (DAC) 415, a comparator 417, a flip-flop 419, and a control switch 421 (to control operation of projection lamp 126), and operates background lamp driver 416 (with DAC 415A, comparator 417A, flip-flop 419A, and control switch 421A) to control operation of background lamp 176. These drivers are used in conjunction with sensors 406 and 408 to effect light level control.

Engine controller 26 also operates fan 420 (Radio Shack 12 VDC fan) to cool the interior of engine controller 26.

Stepper motor 184 and its associated controller operate the focus trombone assembly 233 (carriage 238, with mirrors 160, 162). Trombone assembly 233 allows a constant distance to be maintained between the projector lamp 126 and the location on the interior surface 18 of bowl 20 pointed to by turret assembly 213. Trombone assembly 233 position is initialized by driving it to a mechanical stop.

Each stepper motor controller has two controls: direction (DIR) and clock (CLK). Each clock pulse applied (ON CLK) causes the motor to move one step in the DIR direction. The controllers are hardwired for half steps. The motors are two phase stepper motors with 800 half-steps/revolution (or 0.45 degrees/half-step).

Neutral density filter 152, stepper motor 182 and its associated controller 436, and optointerrupter 156 operate as follows. Neutral density filter 152 (NDF) is a film disc (varying in neutral density around its circumference). The (spot) light beam passes (orthogonally) through NDF 152 which attenuates the light beam. The rotational position of NDF 152 determines the brightness of the spot on bowl 20. NDF 152 is turned by stepper motor 182. Stepper motor 182 and its controller 436 operate as described for trombone assembly 233. The position of NDF 152 is initialized using optointerrupter 156 and circular hole 154 in NDF wheel 152. The optointerrupter 156 is positioned at the outer edge of the filter wheel 152. When hole 154 on NDF 152 passes through the optointerrupter 156, an edge (half of a pulse) is created which signals the HC11 microcontroller 400 that NDF 152 is at a known position.

Azimuth stepper motor 188 and associated controller 430 function as follows. The azimuth assembly (gimbal system 74) determines the horizontal position of the spot on the bowl 20. Its position is initialized by driving the assembly to a mechanical stop. Stepper motor 188 and controller 430 operate as described for trombone assembly 233.

Elevation stepper motor 192 and controller 432 activate the elevation assembly (mirror 82) which determines the vertical position of the spot on the bowl 20. Its position is initialized by driving the assembly to a mechanical stop. Stepper motor 192 and controller operate as described for trombone assembly 233.

Aperture (pinhole) disc 140, stepper motor 180 and associated controller 438, and optointerrupter 142 operate as follows. Aperture disc 140 contains precisely sized holes 138 (apertures). Aperture stepper motor 180 rotates disc 140 so that one of the apertures 138 is positioned in the light beam. The selected aperture 138 determines the size of the spot on bowl 20. Stepper motor 180 and controller operate as described for trombone assembly 233. The position of aperture disc 140 is initialized using optointerrupter 142, as described for NDF wheel 152.

G. Eye Tracker Circuitry

Figure 17:
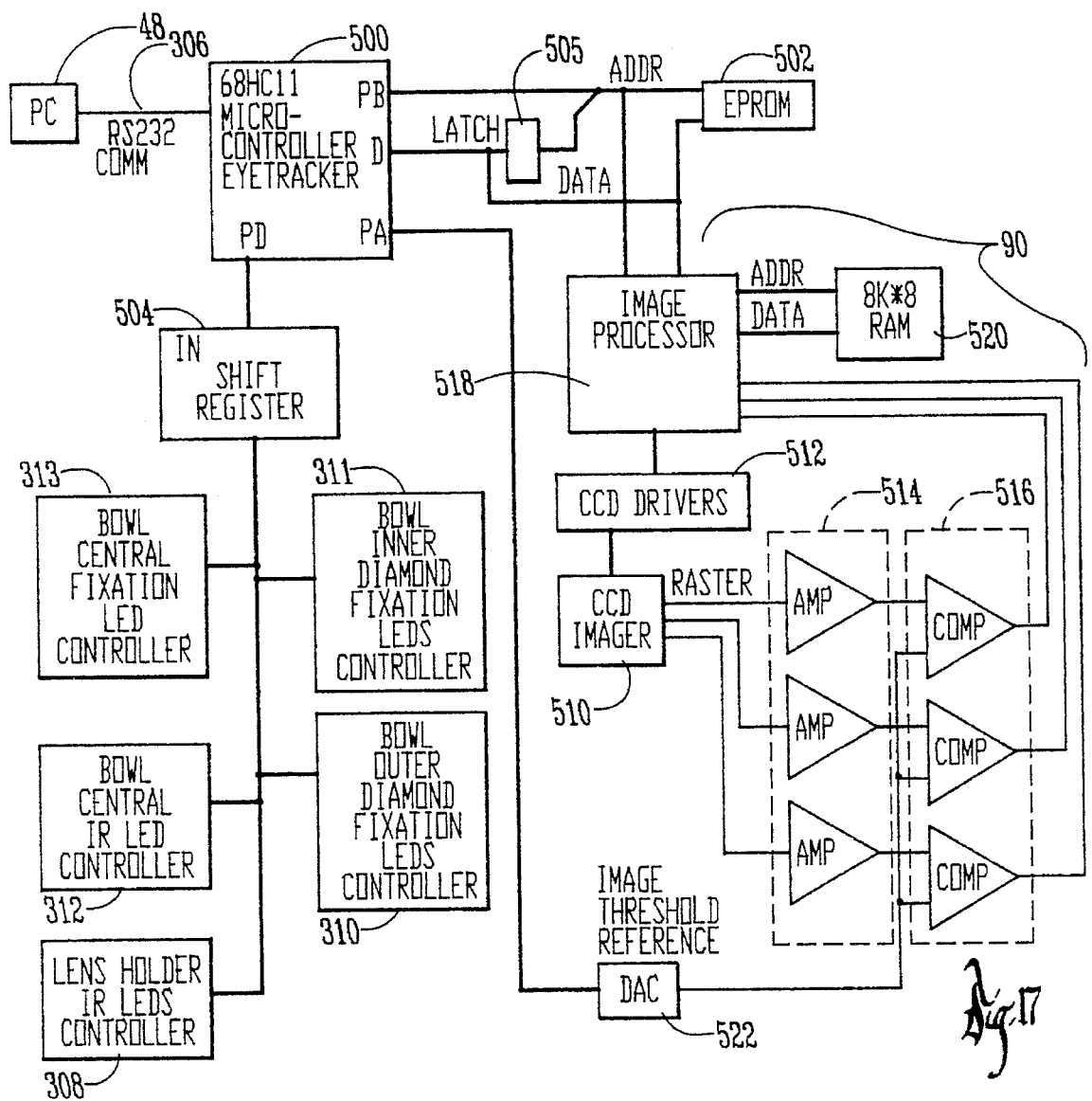
FIG. 17 is a more detailed block diagram of the eye tracker (ET) of FIG. 15 according to the apparatus of the present invention.

FIG. 17, in comparison, provides a block diagram of the specific circuitry of the eye tracker 30 of the apparatus. Eye tracker 30 also utilizes an HC11E2 microcontroller (reference numeral 500—Toshiba TMP 68HC11E1T in association with external address latch 505, EPROM 502, and shift register 504). FIG. 17 shows that microcontroller 500 communicates with PC 48 via RS232 pass-through link 306. One portion of the eye tracker circuitry (controllers 310–313) operates central fixation LED 96, as well as the diamond pattern fixation LED's 100 and 102. That portion also operates the central bowl IR LED 302 (via controller 312). Eye tracker 30 also operates controller 308 which in turn operates lens holder IR LEDs 300. All LEDs 96, 100, 102, 300, and 302 are controlled by the indicated on/off controllers 308, 310–313 as also shown in FIG. 15.

Another portion of the eye tracker circuitry involves imager system 90. CCD imager 510 (Texas Instruments TC245-40 (with socket)) receives the image of the area surrounding the patient's eye. CCD drivers 512 (parallel driver, Texas Instruments TMS 3473B, and serial driver, Texas Instruments SN28846, not shown) drive the imager 510. A collection of operational amplifiers 514 and comparators 516 are interconnected between imager 510 and a field programmable gate array which serves as image processor 518 (Actel A1020A-PL68C). Image processor 518 communicates with a RAM memory 520. An image threshold reference device 522 (a digital to analog or D/A converter) is connected between microcontroller 500 and comparators 516. This entire arrangement allows continuous capture and data compression of the non-constant image of the pupil of the patient's eye that then can be transferred to microcontroller 500. That information in turn is then transmitted to PC 48 for processing. This differs from the qualitative fixation verification methods of other perimeters, e.g., visually checking the patient's eye, periodically rechecking the patient's blind spot; and thus deriving on average level (or quality) of fixation for the entire duration of the test. No information about quality of fixation during individual stimulus presentations is possible with those perimeters.

For further information regarding the nature and makeup of the CCD imager, drivers, and processor circuits, reference can be taken to co-pending, commonly-owned U.S. Ser. Nos. 07/775,194 and 07/867,313, filed Oct. 13, 1991 and Apr. 10, 1992 respectively, which are incorporated by reference herein.

H. Hardware/Software Overview

FIG. 15 also sets forth a block diagram of the hardware/software interface according to the apparatus. As can be seen, PC 48 includes, as standard known in the art peripherals, display screen 530, keyboard 532, mouse 534, printer 536, and memory disks 538 (hard drive and floppy drive). PC 48, in the apparatus, is an IBM compatible PC such as is known in the art (for example, 80486 processor running at 33 MHz, 4 MB RAM including extended RAM, 100 MB hard drive, 5.25" at 1.2 MB or 3.5" at 1.44 MB floppy drive used for installing updates and export/import of data, an RS232 port capable of operating at 14.4K baud, a mouse port or extra serial port, associated cable linking engine controller 26 and eye tracker 30, and one Centronix port and associated cable for linking to local printer 536). All of the peripherals are standard off-the-shelf items.

FIG. 15 shows that PC 48 communicates directly with engine controller 26 and eye tracker 30 (via RS232 link 46 and RS232 pass-through 306). Software associated with PC 48, engine controller 26, and eye tracker 30 allows a variety of functions.

Test results can be stored in a common database accessible by a conventional data base program. PC 48 can also read "results" disks from other perimeters and store those results in the database.

The computer system of the apparatus is network compatible, allowing access to test results of other computers or remote printer use. Software upgrades can be simply sent to users for self-installation using the floppy disk drives.

With respect to engine controller 26, engine controller 26 operates shutter 146 and aperture 138 (via the pin hole wheel 140) to provide a periodic light spot to be projected to the interior of the dome. Patient button (or switch) 40 on the other hand provides a stimulus response from the patient to engine controller 26. Engine controller 26 also controls the operation of projection lamp 126 and background and ambient light lamp 176 by utilizing information from detectors 406 and 408 which sense the output of lamps 126 and 176 respectively.

Engine controller 26 controls operation of neutral density filter wheel 152, focusing of the spot by virtue of trombone system 233 involving mirrors 160 and 162, and the elevation and azimuth positioning of the spot by operation of gimbal system 74.

In comparison, eye tracker 30 controls all of the fixation and illumination LED's as well as operation of imager system 90 and communication of the information received by imager system 90 to PC 48.

The general structure, electronic circuitry, and hardware/ software interface have now been described. It is to be understood that the precise specific makeup of circuitry and software can take many forms. A description of the general operation of the invention will now be set forth.

I. General Operation of Apparatus

Initially the apparatus is moved into a position at or near where patient 38 will be seated. RS232 link 46 is connected to stand-alone PC 48 that has appropriate software installed on hard disk 538.

Initialization of the perimeter program is then accomplished on PC 48 including, for example, entering identification information regarding patient 38 and selecting the type of testing desired.

Patient 38 optimally would be seated in a comfortable position. The apparatus would be moved to an approximate position relative to patient 38. Face plate 10 would then be swung to patient 38 and vertically adjusted to the patient's head. The operator would accomplish this by swinging dome 20 away from face plate 10 and directly viewing the patient's head.

Fine adjustment of face plate 10 to the patient's head would then occur by vertical adjustment of face plate 10 on pole 34, placement of the patient's chin in chin rest 14, and then fine adjustment of chin rest 14 and forehead rest 16. If needed or used, lens holder 60 could then be adjusted to the patient's eye 86 to be tested. Sliding hinges 24 allow dome 20 to be centered right and left in front of the patient's eye 86. Either eye may be selected for testing. Manual horizontal positioning knob 62 (see FIG. 2) is used for this purpose.

Once patient comfort and alignment are generally confirmed, dome 20 can then be latched to face plate 10 (using latch and receiver 64 and 66). Testing begins by double checking alignment of patient 38. PC 48 would initiate a testing procedure whereby eye tracker 30 would capture an image of the patient's eye 86. Fixation LED's (96, 100 and/or 102) would be operated to present an area of fixation for the patient's eye. If fine tuning of vertical height is needed, it can then be accomplished by turning chin height adjustment wheel 84. Fine-tuning of horizontal position is accomplished with knob 62. Position is verified using eye tracker 30.

Patient 38 is then handed patient switch 40 and instructed to fixate, usually on center fixation LED 96. PC 48, according to software, would coordinate several processes which are simultaneously active including:

1. Moving engine controller 26 motors 188, 192 to position a visual stimulus in dome 20.
2. Presenting the stimulus by opening and closing engine controller shutter 146.
3. Monitoring the patient's response via patient switch 40.
4. Monitoring and controlling the ambient dome light by controlling engine controller background lamp driver 416 using sensor 408.
5. Monitoring/controlling the spot brightness by engine controller projection lamp sensor 406 and driver 414.
6. Monitoring patient's pupil size and position with eye tracker 30 imaging system 90.
7. Updating display 530 of PC 48 as the test progresses.
8. Responding to operator requests (for example "pause").

During testing, PC 48 therefore keeps track of where each visual stimulus is presented on dome 20, the response of patient 38 to each stimulus, and whether (via eye tracker 30) patient 38 was sufficiently fixated to render that correlated result valid. A variety of different test result formats can be prepared by PC 48. Basically a mapping of location of stimulus and patient response would be prepared. This could be evaluated by a trained practitioner to evaluate a patient's visual field.

A very important advantage of the present invention is the ability to verify on a stimulus-by-stimulus basis the validity of patient responses. The present invention eliminates periodic verification testing such as, for example, placing a visual stimulus in a patient's blind spot at various intervals, requiring the operator to periodically visually check if the patient is fixating, or requiring the operator to watch a video screen to check if the patient is fixating. Fixation validation is performed essentially automatically and continuously.

J. Description of Software Operation

The following will be a general discussion of operation of the apparatus in the context of software related to PC 48, and firmware related to engine controller 26 and eye tracker 30. It is to be understood that the software and hardware can take many different configurations such as is within the skill of those skilled in the art. The functions available with the software control are similar to existing automated perimetry testing and results options. Those skilled in the art understand the various terms and procedures for those functions and tests. The description below will set forth in general terms how these functions are accomplished with the apparatus.

As previously described, the perimeter electronics of the apparatus consist of three separate subsystems: an IBM compatible personal computer (PC 48), engine controller (EC 26) and eye tracker (ET 30). EC 26 is an HC11 microcontroller based system which presents the stimuli (spots) to patient 38. ET 30 is also HC11 based and captures and processes images of the patient's pupil. The three systems communicate over a single (bi-directional) RS232 serial communication link 46. EC 26 and ET 30 are slaves to PC 48. They accept and execute commands issued by PC 48. The transfer of data back to PC 48 is done at the PC's request (polled). The following describes the EC and ET firmware, the PC software, and how these three sub-systems operate together to perform perimeter tasks.

In partitioning tasks to the three processors, the design philosophy has ET 30 and EC 26 perform only the most rudimentary tasks on their own (e.g. "move the azimuth motor +100 pulses" as opposed to "present a spot of size 5 at location 30,30"). This allows the greatest flexibility with respect to changes and upgrades. The more intelligence partitioned to PC 48, the greater the ability to do fixes and upgrades, since these can be done via a software change instead of a firmware change. This may mean the difference between sending a floppy disk to the user and requiring that the entire EC 26, for example, be sent to the factory (or simply choosing not to do the upgrade).

1. Engine Controller Firmware

The EC firmware consists primarily of code to implement a set of commands issued by PC 48. These commands mainly control the EC's peripherals: motors, ADCs, DACs, and switches (as described previously). PC 48 issues a command which is queued in HC11 RAM. The HC11 (processor 400) continually executes commands from this queue. Some commands result in data to be passed back to PC 48. PC 48 polls the HC11 400 for this data. The command set to accomplish this is within the skill of those skilled in the art.

By referring to FIGS. 15 and 16, the relevant electrical and mechanical components of the apparatus which are operated by engine controller 26 are illustrated. The engine controller firmware controls stepper motors 180, 182, 184, 188, by issuing instructions to each motor's independent direction and clock signal lines. The firmware also includes self-test and error checks. The firmware also has the advantage of flexibility, since its operation can be changed by reprogramming of EPROMs.

PC 48 has a command set which it can send to engine controller 26. The commands include requests for information to which EC 26 responds (for example, motor status, information regarding the patient switch 40 such as time at which it is pressed and time at which it is released, projector and background light intensity from light sensors 406 and 408 via their analog to digital converters, and other status information—see FIG. 16). Finally, the PC 48 can send commands which in turn result in action by engine controller 26 (for example, movement of motors to new positions, system initialization, background and projector lamp light level adjustment, stopping of the motors, and self-tests). Default parameters can also be sent from PC 48 to engine controller 26.

It is to be understood that system programming will instruct engine controller 26 as to the brightness, size, and position of the light spot from moment to moment. All these components must therefore work together to achieve the desired manipulation of the light spot. As can be appreciated, this requires quick and accurate operation of stepper motors. Programming takes into account the acceleration and deceleration of the stepper motors during their operation by building in delay times to accommodate the same. Delay times are related to the number of pulses sent to the motor and the direction of rotation. It is also to be understood that the programming can issue instructions to vary the time period between presented stimuli to deter anticipation by the patient.

The motors are commanded in sequence by queuing commands. Essentially PC 48 gives each motor controller a sequence of two movements, namely, first, the command to move the motor by a first amount and direction, and then second delay some number of milliseconds. The next command is sent to move the motor by a second amount and direction.

2. Eye Tracker Firmware

ET 30 has one primary task: continually capture and process pupil images and pass the results to PC 48. PC 48 initiates this activity by sending a command to ET 30. PC 48 also sets (via commands) the ET's 30 hardware initialization parameters. Part of the initialization process includes determining the proper image threshold (to convert from a gray-scale image to a binary image).

Twelve times per second the following sequence occurs:

(a) CCD imager 510 captures an image of the pupil.

(b) image processor 518 run-length-encodes the image.

(c) HC11 microcontroller 500 processes the run-length-encoded image to extract the pupil position and size.

(d) HC11 microcontroller 500 sends (upon request) the pupil size and location to PC 48.

(e) fixation LEDs 96, 100, 102 and IR LEDs 300 and 302 are controlled by PC 48 via commands sent to ET 30.

CCD imager system 90, and its associated components in eye tracker 30 have been previously described. By referring to FIGS. 15 and 17, specific interconnection between electrical and mechanical components for eye tracker 30 are shown. Eye tracker 30 controls operation of all fixation and infrared LEDs. LEDs 96, 100 and 102 give fixation targets for the patient. The lens IR LEDs 300, and central bowl IR LED 302 are directed towards the patient's eye to illuminate the eye adequately for eye tracker image processing without disturbing normal perimeter operations. More importantly, eye tracker 30 also keeps continuous, real time surveillance of the patient's eye in coordination with the perimeter testing procedures. This provides highly accurate and reliable information to the system regarding the patient's fixation and eye blink during each projected light spot. This monitoring capability may also be useful for other testing procedures developed in the future.

CCD imager 510 supplies a standard video output signal to its image processor 518. Image processor 518 utilizes 68HC11 microcontroller 500 and a field programmable gate array or FPGA (custom programmed for digital image compression), a RAM buffer for data storage, and video input circuitry to amplify, synchronize and threshold the analog CCD signal. Controller 500 communicates with PC 48 via a 14.4K baud serial port and allows PC 48 to command a variety of operations, generally set forth below:

1. on-off control of visible and infrared LEDs (96, 100, 102, 300, 302) in dome 20;

2. capture and process a field of video data from CCD imager 510;

3. set/adjustment of processing parameters;

4. execute pupil-finding algorithm on run length encoded data;

5. transfer packets of "result" information to PC 48.

The run length encoding, such as is known in the art, is used for image compression, such as is also known in the art. Controller 500 first forms a binary representation of the standard digital image by comparing the gray level of each pixel of the image to a given threshold value, then replacing its gray level with a digital "one" or a digital "zero" depending on whether or not it exceeded the threshold. Secondly, it converts the binary image into a set of "runs" by going through the image row by row from top to bottom. A group of consecutive pixels within a row with a "one" value (or "zero") are termed a "run" and the location (column number) of the first and last pixel along with the row number are stored to represent the run. Filtering may be introduced by requiring a minimum number of pixels in a run or between runs.

The thresholding operation is done in the analog video front end of image processor circuit 518 based on a value programmed by PC 48. This value is referred to as the DAC threshold because it undergoes digital/analog conversion before being used to threshold the video. Its programmed digital value is in the range of 0 to 255. The second part of run length encoding (conversion to runs) is performed on the fly by the FPGA Actel A1020A-PL68C as controlled by microcontroller 500.

Eye tracker 30 firmware utilizes packets (containing a ten byte data structure) which contain relevant information of a given processed image field. The packets are sent from image processor 518 to PC 48 by microcontroller 500 when requested by PC 48. The packets contain:

1. x-position or column number in pixels of the center of the pupil (two bytes);
2. y-position (row number) in pixels of the center of the pupil (two bytes);
3. radius of the pupil in y pixels (two bytes);
4. count in video fields since time set by PC 48 (two bytes);
5. number of runs in image divided by two (one byte);
6. general status information (one byte).

Controller 500 may operate in either a continuous acquisition mode in which packets are queued in the RAM buffer for access by PC 48, or an "acquire as requested" mode where a single packet is generated and sent per PC 48 request.

A particular concern to eye tracker 30 is to correctly locate the patient's pupil. In the apparatus, pupil finding (also referred to as circle finding) is performed by controller 500 on the run length encoded data to determine the exact position and size of the pupil in the image. This is done by first identifying a group of runs in the image which collectively have certain characteristics associated with those of the pupil, then verifying that they actually represent a pupil (or other round dark object) by performing circularity analysis.

The initial association characteristics for the group are as follows:

1. Must have a long run which is greater than the minimum and less than the maximum acceptable pupil diameter as defined by PC 48 during an initialization period.
2. Must have at least X small runs directly above and below the long run. These runs must be continuous (i.e. not separated by any blank rows). The value of X is based on the programmed minimum pupil diameter.

Because an object which meets these criteria may not be necessarily circular and therefore not a pupil, the circularity analysis as mentioned above is followed consisting generally of:

1. Using trigonometric properties, finding the circle which includes the two end points of the long run and one end point of the top run in the object.
2. Finding two other points on opposite edges of the object midway between the long run and the top run, and finding the two circles which include each of these points (one at a time) and the two end points of the long run.
3. Comparing the positions of the centers of the three circles. If they are within the maximum acceptable variation (programmed by PC 48) of each other, declare the object a pupil and report the features of the first circle in the result packet described above.

Identification of the initial group of runs requires a search of the image, starting with the first run at the top left of the image and proceeding in the same order that the runs were stored (left to right, top to bottom). When a set of runs which meet the association criteria are found the search is paused and the circularity analysis performed. If successful, the pupil size and position are stored in a packet and the algorithm is complete. Otherwise the search continues where it left off and the entire process is repeated. This search and verify loop executes until the pupil is found or all of the runs in the image are exhausted.

The speed and robustness of the algorithm are significantly enhanced if the pupil is the first dark roundish object encountered during the search. This goal is aided by mounting CCD 510 upside down so that, for example, most of the upper eyelashes are below the pupil in the image.

Autothresholding is the process of determining an optimal DAC threshold value for a given image, where an optimal value is defined as one at which the pupil is "solid" but not accompanied by excessive extraneous runs. Solid implies that the runs which represent the pupil are predominantly singular from edge to edge of the pupil (i.e. not segmented or broken up). The range of acceptable threshold values for any given image is somewhat qualitative and varies from case to case, but generally there are 10 to 15 values which will work adequately.

The code which implements the autothresholding function is located on PC 48. The algorithm is an iterative process which employs a software loop consisting of three basic elements:

1. Command 68HC11 microcontroller 500 to grab an image field, process the data, and send the result packet to PC 48,
2. Analyze relevant information from the packet,
3. Adjust and set threshold value based on the analysis.

The threshold value is initially set to zero, then adjusted for each pass of the loop based on a set of logical statements which use the number of runs in the image and the radius of the pupil (if found) as follows:

1. If the number of runs is less than ten and a circle has not been found, increase the threshold value by 10. This is usually the case initially when the threshold is much too low, and allows the value to be moved rapidly to the point where data begins appearing.
2. If the number of runs is greater than ten but no circle is found, increase the threshold by 4. This is an intermediate stage which prevents overshooting the optimal range.
3. If a circle is found but its radius is at least four pixels greater than or less than that of the most recent previous circle, increase the threshold by 2. This is normally the case when the pupil starts to fill in and does not yet produce a consistent circle.
4. If none of the above is true and the circle is found four times consecutively, the algorithm is complete.
5. Once the first circle is found, if the loop executes ten times without finding valid circles the threshold value is reset to zero, restarting the algorithm.

The speed of the autothresholding algorithm is dependent on where the final threshold value lies within the 0 to 255 gray level scale range. In general, completion of the algorithm will require 15 to 20 passes of the software loop. During autothresholding, image processor 518 operates in an "acquire as requested" mode. The total time for each loop pass is approximately 200 ms resulting in a total execution time of 3 to 4 seconds for the algorithm. The constant video rate of CCD camera 510 is 38 fields per second or 26.3 ms per field. Based on timing tests on a variety of test images and real eyes, the pupil finding algorithm on 68HC11 microcontroller 500 takes from 10 to 40 ms to execute on a field, depending on the amount of non-pupil runs (lower eyelashes, etc.) in the image. Therefore, in its continuous acquisition mode of operation, eye tracker 30 can process every third image field for a rate of 12.67 fields per second. In this mode, the 68HC11 (500) queues the result packets in its RAM buffer for PC 48, which may request the packets one at a time and will receive them in the order stored (first in, first out). The queue can hold up to 20 packets allowing for 1.578 seconds of data storage before packets are overwritten (oldest first). To avoid loss of data, the overall processing rate on the PC side (receive and display packet information) must be greater than 12.67 packets per second.

Figure 19:
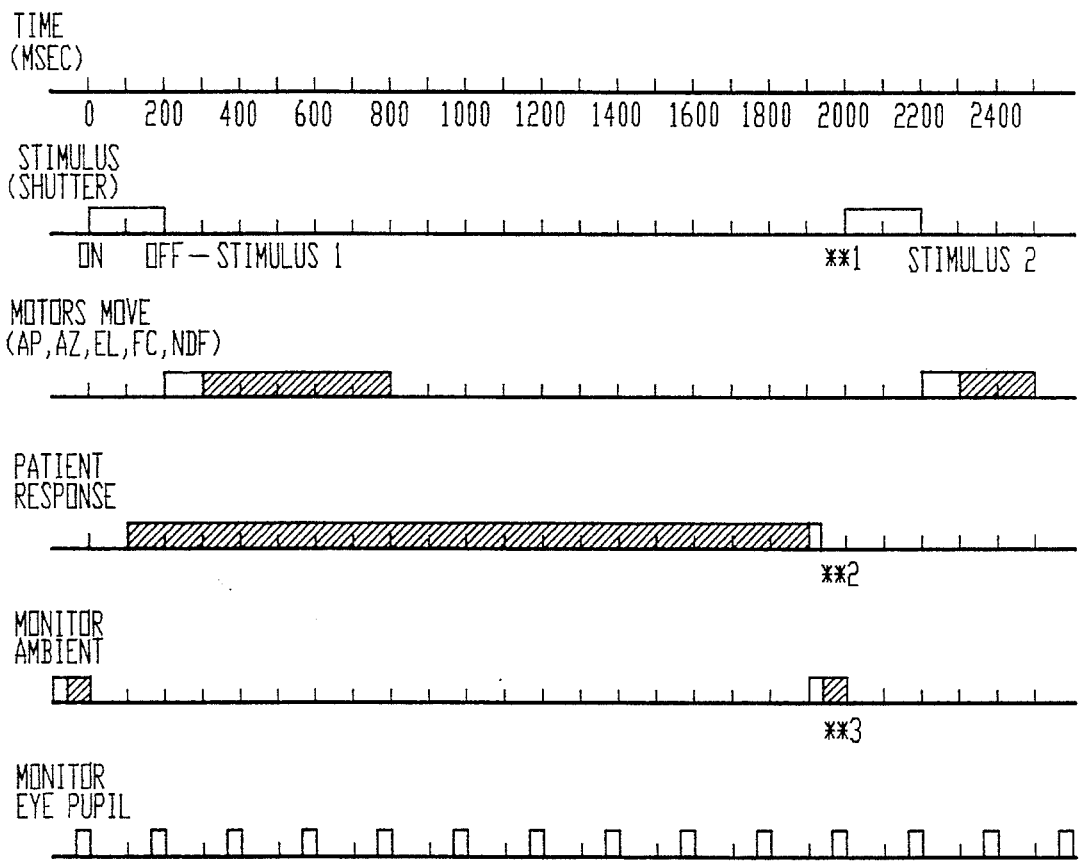
FIG. 19 is a timing diagram illustrating the functioning of the software and perimeter components.

FIG. 19 illustrates generally the timing sequence of stimulus display. It shows the relationship between shutter opening (to allow the stimulus to be displayed on dome 20), patient response (via patient button 40), and motor movement. It also shows ambient light and pupil monitoring.

3. Personal Computer Software Architecture a. Generally

The PC software performs the following perimeter functions:

1. Provides the clinician or operator interface to the apparatus,
2. Controls the execution of a test,
3. Performs data management on patient and test-results data,
4. Performs test-results analysis and presentation (display and print).

The software was implemented using several commercial programming tools and employs some of the most recently developed programming philosophies and techniques. By referring to FIG. 18, the general software structure can be seen.

Software for the invention can be described as a system of co-executing FSA's (finite state automata). Many of these FSA's are stored in Paradox (a commercially available database program) files—see FIG. 18. The specific contents of some FSA's are dependent on what the current test and strategy type is during operation of the system. The FSA's are essentially control blocks of code, each of which controls an aspect or aspects of the operation of the apparatus. These control blocks are stored in the Paradox database tables or are otherwise accessible. Each Paradox-stored FSA has a description file, a Paradox Table, a coding object, and FSA communications, the latter of which is basically a table which instructs how messages should be routed to or from other FSA's. Other tables list the various possible states, events, conditions, and/or actions for the FSA. The architecture of the software is setup as follows. Each FSA is defined by its current state. The state is defined by set of FSA contents and their associated current states. What are called actions are determined by what are called events that occur in various FSA's. Nearly every one of the FSA's is loaded to run time from a Paradox Table. There are some processes, however, which are not FSA driven.

b. The Windows Environment

The apparatus software was developed to run under the Microsoft Windows (see 602, FIG. 18) operating system on PC 48. Windows has a graphical user interface (GUI) 606 and is able to support the GUI requirements of the perimeter operator interface.

The software makes extensive usage of the Windows 3.1 API (Applications Program Interface) services for user interface functions and to display or print test results. DOS 5.0 (Microsoft) and BIOS provide the PC component management facilities. Windows 3.1 provides the working environment/shell. It also manages GUI interface 606 to the user by providing the API functions for the software to access system resources such as keyboard and mouse input and screen output. Windows also provides the timer resources which are used to run the test software. The system can be connected to a network using a network interface card. Word for Windows 2.0 (Microsoft) allows text editing.

The programming language used was Borland Turbo-Pascal for Windows 1.5. The program style used is object oriented programming (OOP), which incorporates data and routines which operate on that data into a structure called an object. Other tools and vendor packages used include Paradox 3.5 by Borland, Archimedes C compiler, 68HC11 assembler and linker, and Make Utility by Poly Make.

The actual interface between the program and the Windows API is buffered through the use of OWL 600 (Object Windows Library, which is distributed with the Turbo-Pascal compiler). This library (or collection of objects) encapsulates the native API functions. The programmer's interface to the Windows API is rather terse and OWL allows a higher-level (and therefore, hopefully, simpler) interface than would be possible in interfacing directly to Windows. The Object Graphics Library (OGL by Whitewater) 604 is a software development package which simplifies the program's interface to Windows graphics functions. This can be considered an add-on to OWL 600 which provides higher-level-still functions for drawing to screen 530 or printer 536.

c. Clinician Interface

The software uses GUI interface 606 to enable the viewing of both graphics and textual data through the same visual port. This gives the clinician a unified and simple access to all the needed data and parameters. It further facilitates simultaneous viewing of results in different formats and simplifies and unifies presentation of reports on either computer display 530 or printer 536.

Figure 21:
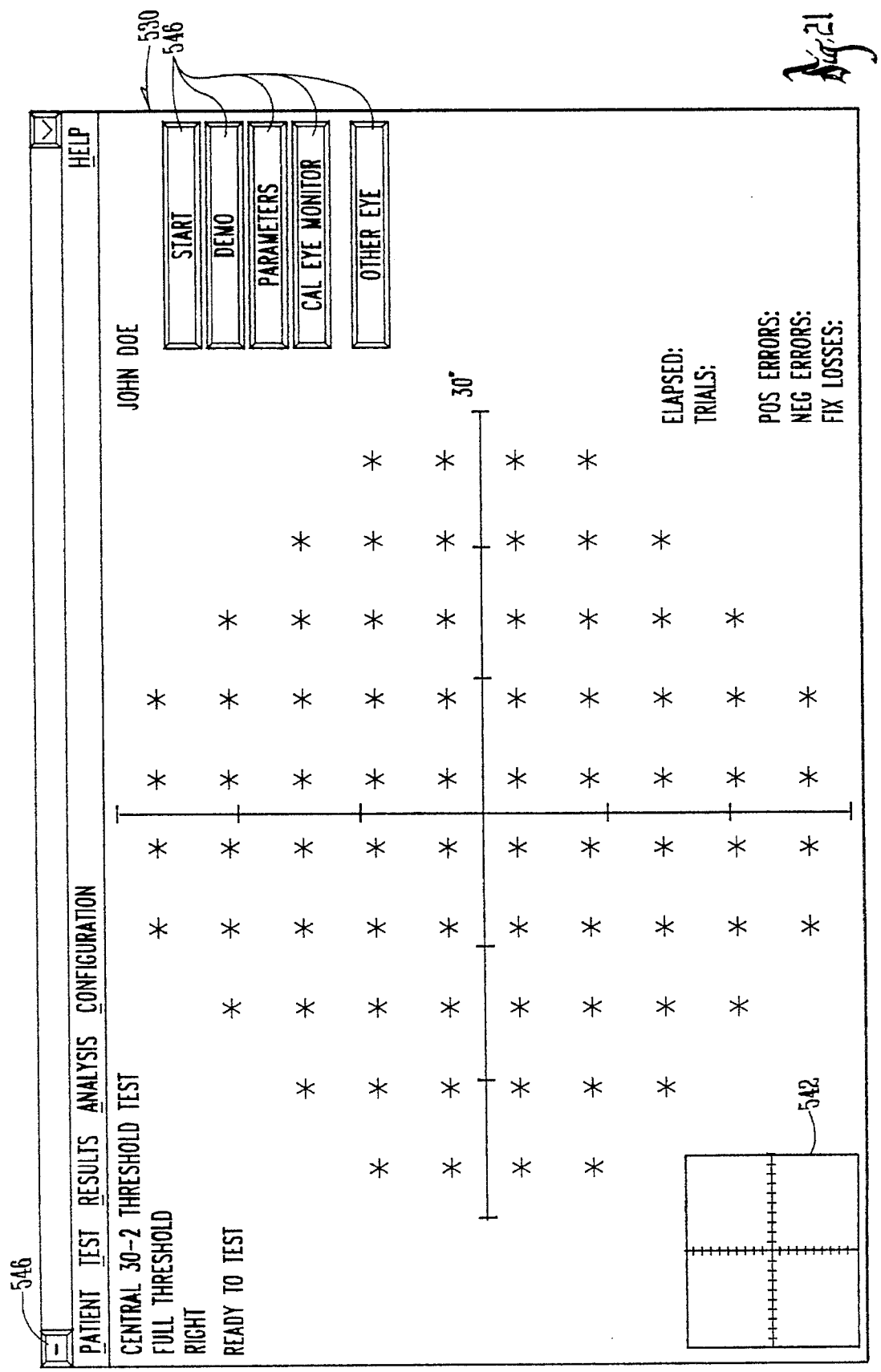
Figure 22:
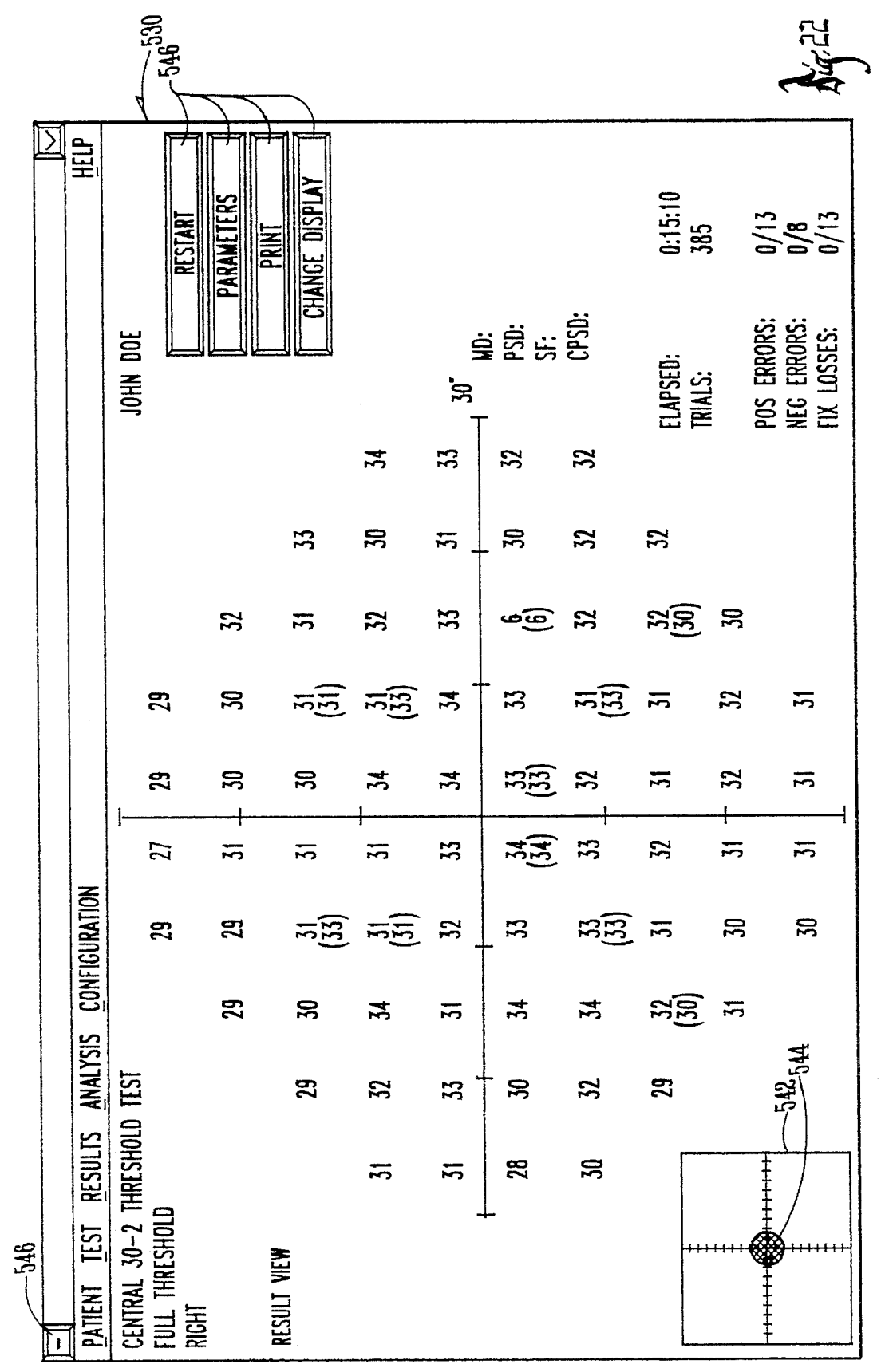

Windows is the underlying system platform used to achieve this flexible interface. Various user interface screens are possible. Examples are shown at FIGS. 21 and 22 and are implemented as windows. It is through these that the clinician can view results and alter parameters and patient information. It is also via these that the clinician controls the patient testing and performs configuration and routine maintenance tasks.

Graphics user interface (GUI) 606 under Microsoft Windows therefore makes the software very user friendly. The patient and result data bases are implemented using Paradox tables so the results may be easily analyzed using other standard software tools.

The clinician navigates through different windows and screens using mouse 534 and/or keyboard 532. Mouse 534 is most usually used as a pointing device although other such devices could be substituted (for example, a track ball or a joy stick). Mouse 534 can be used for starting actions by selecting corresponding buttons (see reference no. 546, FIG. 22) used on display 530 for selecting fields to be edited. Alternatively keyboard 532 could be used to "tab" to the desired selection. In general, controls are most easily accessed using mouse 534 (e.g. list boxes, combo boxes, check boxes, scroll bars), but it is possible to access all controls purely through keyboard 532. Text entry fields require using keyboard 532, but mouse 534 may be used for selection and highlighting text.

The clinician controls the processes and tests via windows screen 530, mouse 534, and keyboard 532. The clinician can access patients' information and their test results by selecting appropriate menus and buttons. The testing is also accomplished in this simple manner. At any stage of testing and general usage, screen 530 will present the clinician with only those choices which are pertinent and available at that time.

The following files must be installed preferably in a separate sub-directory e.g. C:\perim:

Perim.exe—the main program file.

Commlib.dll—the communication DLL used to communicate with EC 26 and ET 30.

Pxengwin.dll—the Paradox engine for windows DLL.

Perim.ini—the configuration file in the windows directory.

*.db, *.px—the Paradox tables (data base files).

The *.db files are all standard Paradox 3.5 tables that can be edited using Paradox 3.5 or higher versions.

The software therefore allows tests of retinal sensitivity which functionally and visually are comparable and compatible with other automated perimeter instruments. The tests which are incorporated include the standard thresholding and screening tests, as well as automatic diagnostic tests, and kinetic tests. It also enables the user to design custom tests for screening and full threshold strategies.

In the threshold tests, full threshold, full threshold from prior data, and fast threshold strategies are available. Screening tests, including threshold related, quantify defects, three zone, and single intensity strategies are also available. Standard spot patterns are available. The automatic diagnostic test is available for static perimetry; kinetic perimetry can be performed using the manual random, auto test, and custom scanned test modes. All these types of tests, and more, are available with the invention and are known in the art.

Various reports available with the system may be displayed on screen 530 or sent to printer 530. Context sensitive help is available at each stage.

Defining customized tests is done by graphically drawing the required pattern on the screen using mouse 534. Alternatively new test patterns can simply be added to relevant Paradox tables and new strategies and test flows can be declared.

The software also enables importing results from other compatible automated perimeters to allow the practitioner to maintain all related records for one patient from one location.

The perimeter test run is controlled by the clinician using buttons displayed on screen 530 at various stages. Once the test is started the system will stimulate the patient using a spot size selected from the "parameters" programmed into the software. The system will threshold the fovea, determine the patient's blind spot location, and then test the rest of the spots as defined by the spot pattern and test strategy defined in the parameters.

Three standard analysis functions are available under the analysis option of the main menu, namely compare, average, and merge. Under the compare selection, two results of the same test strategy type may be compared. The software will do a spot by spot subtraction (first selected minus second selected), and then display the HOV for this comparison. HOV (hill of vision) is a term well known in the art to describe the retinal sensitivity as a function of retinal position.

Under the averaging option, up to 16 results of the same test and strategy types can be selected. The software will average these results by spot by spot averaging and display the HOV for the average.

The merge option enables up to five results of complimentary test and strategy types to be selected. The software will generate a set of all the spots from the selected results and display the resulting HOV.

Test results can be stored in a common database accessible by a conventional database program. PC 48 can also read "results" disks from other perimeters and store those in the database. It is to be understood that statistical analysis software can be used to analyze the results.

4. Specific Software Examples

To provide for a better understanding of the software, by referring to FIGS. 18–22, more specifics regarding the software are now set forth. One skilled in the art will understand how this organization can be incorporated into software to achieve the purposes of the present invention.

a. Text and Database Files

There are two types of files used in the perimeter software: text files and database files (tables).

Text files (perim.ini 610 and attenval.dat 612—FIG. 18) hold calibration data that is unique to each system. These files are read once; when the program is invoked. A text file (export 614) is also used to hold a text version of a series of test results (for custom analysis by a non-database user).

Paradox is a standard commercially available database by Borland. All of the databases (tables) used by the perimeter software are Paradox tables. These tables hold not only information about the patients and their test results, but also hold algorithms for various types of perimeter tests. Test algorithm changes are therefore non-complex (one simply edits the appropriate database as opposed to recoding a section of the software).

Tables (620, 621, 622, 623, 624, 625, 626, 627, 628, 629) are employed for several different functions:

(1) hold the database for all of the patients tested and all of the tests performed on a particular machine.

(2) hold spot patterns for the various tests.

(3) hold the format of the various printed reports.

(4) hold the finite-state-machine definitions (program control and sequencing algorithms) used by the code objects to execute a test.

The Paradox engine dynamic link library (DLL) 630 is a commercial software product used to interface between custom code (as opposed to the Paradox-provided user interface) and the Paradox tables. It is a collection of subroutines (not objects) which are accessible by all programs running on PC 48. It allows the normal database functions to be executed by a program rather than a user. Paradox tables contain FSA's (Finite State Automata) such as previously described and are known in the art.

b. Objects

Objects are a type of self-contained program module (written here in Turbo-Pascal). The objects in the apparatus software contain the code that actually runs the apparatus (e.g. runs tests, analyzes results). The objects communicate by sending messages (within the Windows framework) to each other. An object executes when a message is passed to it. It receives the message and executes the appropriate operation (which may include sending Windows messages to other objects). The perimeter objects are outlined below (see FIG. 18).

Analysis (640)—performs various types of statistical analysis functions on existing test results.

Results (641)—manages the storage and retrieval of existing test results.

Patient (642)—manages the entry, storage, and retrieval of the patient data (e.g. name, date of birth) for all patients tested.

RT_FSA (643)—manages the execution of the perimeter test, including control of EC 26 (e.g. moving motors, presenting spots, recording patient response), ET 30 (e.g.

continually requesting pupil data), PC 48 (e.g. controlling program flow), and interfacing with the operator (e.g. detecting operator input, updating screen 530).

Test loop (644)—controls test/strategy flow, makes stimulus decisions.

Configure (645)—performs perimeter system configuration tasks (e.g. select printer 536).

AmbFSA (646)—maintains the background (ambient) level at a constant brightness during the execution of a test. This is accomplished by reading EC background lamp sensor 408 and adjusting EC background lamp DAC (see FIG. 16) per a closed-loop control algorithm.

ETFSA (647)—when invoked by Timer 643, at each timer tick polls ET 30 for the pupil size and position. See image of pupil 544 in eye tracker window 542 of display 530 in FIG. 22. Each time it receives this information (from ET 30), Timer object 643 displays the information (via OGL 604) in the eye monitor window 542 on the display screen 530.

Report Print Generator (648)—performs the formatting of results or analysis data for report printing or displaying.

The object windows library (OWL) 600 is a collection of objects which allows a program (or code object) to communicate with Windows services 602 at a higher level (than one can communicate directly with Windows services). For example one could create a common type of window (on screen 530) with one command (or object invocation) instead of several (more rudimentary) commands.

Windows services 602 are a collection of objects that perform standard PC functions (e.g. write text in a particular window of the screen). They receive messages from the perimeter code objects and perform the requested action. These are equivalent to "operating system calls" in a non-object-oriented environment.

c. FSA's

The function of the FSA's will now be summarized to allow one skilled in the art to understand how functional tasks are partitioned in the context of the preferred software.

Figure 20:
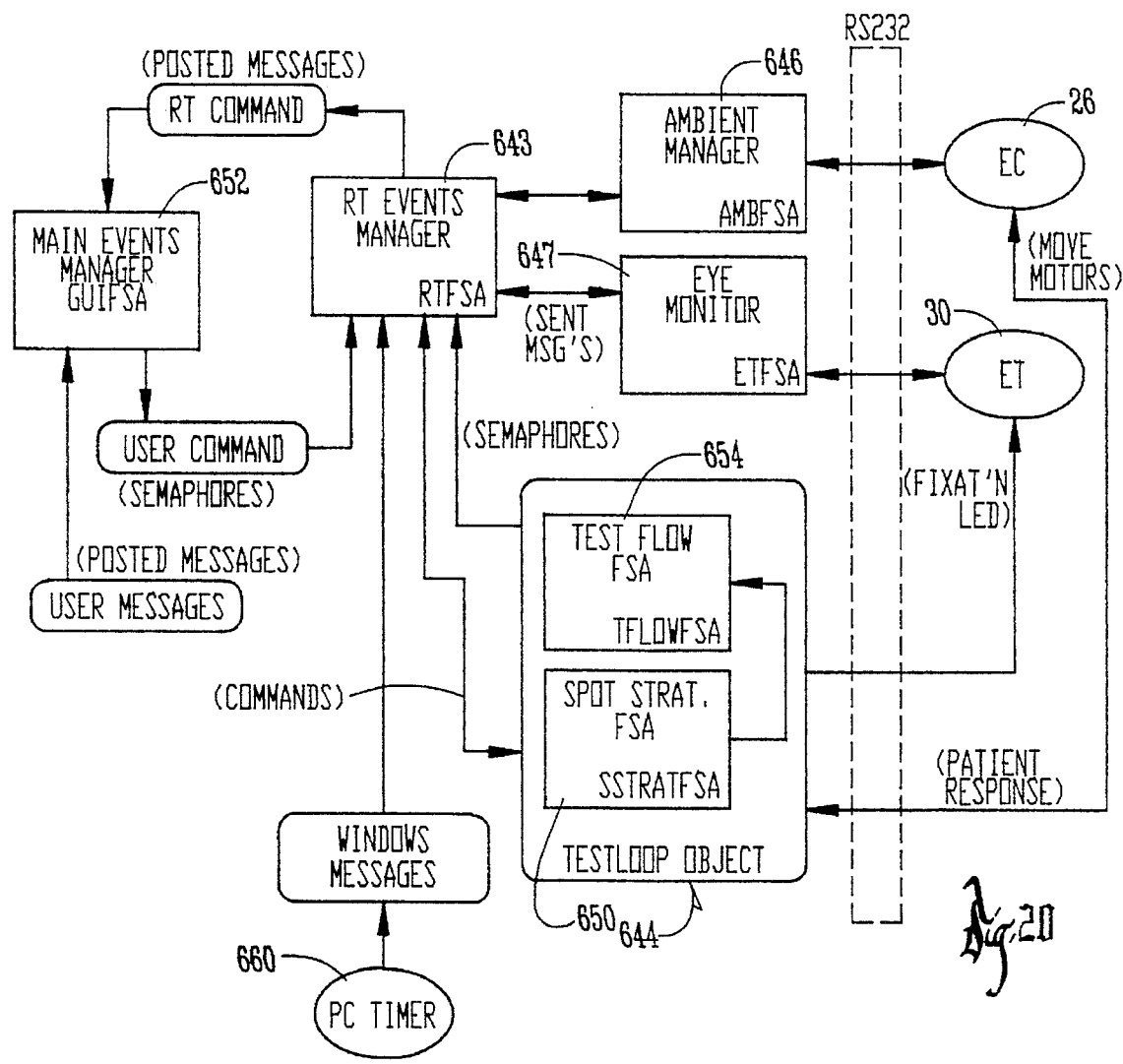
FIG. 20 is a diagram of the flow of messages between certain portions of the software according to the apparatus of the invention.

(1) Main GUIFSA 652 (stored in Paradox table 626, FIG. 20)

(a) Controls which menus and buttons are displayed and enabled on main screen 530;

(b) Controls which static fields are displayed, based on test and strategy types;

(c) Controls actions taken when certain events occur in order to coordinate other FSA's.

These are events which are not generated by the clinician or operator of the perimeter, but by other parallel processes running in the system.

(2) RTFSA (643, FIG. 20)—Timer Tick FSA (Real Time FSA)

(a) Provides the timing for a test run;

(b) Sends commands to engine controller 26 and eye tracker 30 to stimulate, move to next spot, check for patient response, check for patient pause, control background, and check eye pupil position;

(c) Interfaces to the spot strategy 650 and test flow 654 FSA's which determine the spot to test and at which intensity to stimulate;

(d) Interfaces to ambient FSA 646 to monitor/control the bowl background illumination;

(e) Interfaces to eye monitor FSA 647 to control the auto thresholding of eye tracker 30 and to obtain the position and size of the pupil.

(3) TFlowFSA (654, FIG. 20)—Test Flow FSA (a) Controls the order of the states (or states) of a test run. Some major states are fovea resolution, blind spot determination, cardinal spot's resolution, other spot's resolution. States used and their order in a test run are a function of the test flow index, which is in turn determined by the test and strategy types of the test being run. The stages are also determined by various test parameters being enabled.

(4) SStratFSA (650, FIG. 20)—Spot Strategy FSA (a) Determines the spot intensity to be presented for each spot at each stimulus;

(b) Determines how many times a spot should be resolved;

(c) Determines when a spot has been resolved;

(d) Determines when spots should be added and removed from the spots candidate list;

(e) Also keeps track of the increment step size for each spot. The particular FSA used is a function of test and strategy type;

This FSA is called by RTFSA 643 when RTFSA 643 has determined that the patient response has taken place. It is also called when initial spots for a test are placed in the candidate list. It is always to be understood that the particular FSA used is a function of test and strategy type.

(5) AmbFSA (646, FIG. 18)—Ambient Monitoring FSA (a) Controls the bowl illumination so as to maintain it at a constant level;

(b) Does this in a way that is transparent to the test run;

(c) Informs RTFSA 643 if the ambient illumination is out of range;

(d) Informs RTFSA 643 if the ambient illumination cannot be brought into range.

(6) ETFSA (647, FIG. 18)—Eye Monitor FSA (a) Determines the desired imager (eye tracker 30) threshold level for pupil monitoring;

(b) Gets the pupil position and size data from eye tracker 30 and sends it to eye monitor window 542 on the main screen 530 (see FIG. 22);

(c) Performs these functions in a way that is transparent to the test run;

(d) Informs RTFSA 643 if the threshold is out of range;

(e) Informs RTFSA 643 if the threshold cannot be brought into range.

d. Non-FSA Processes

Figure 18:
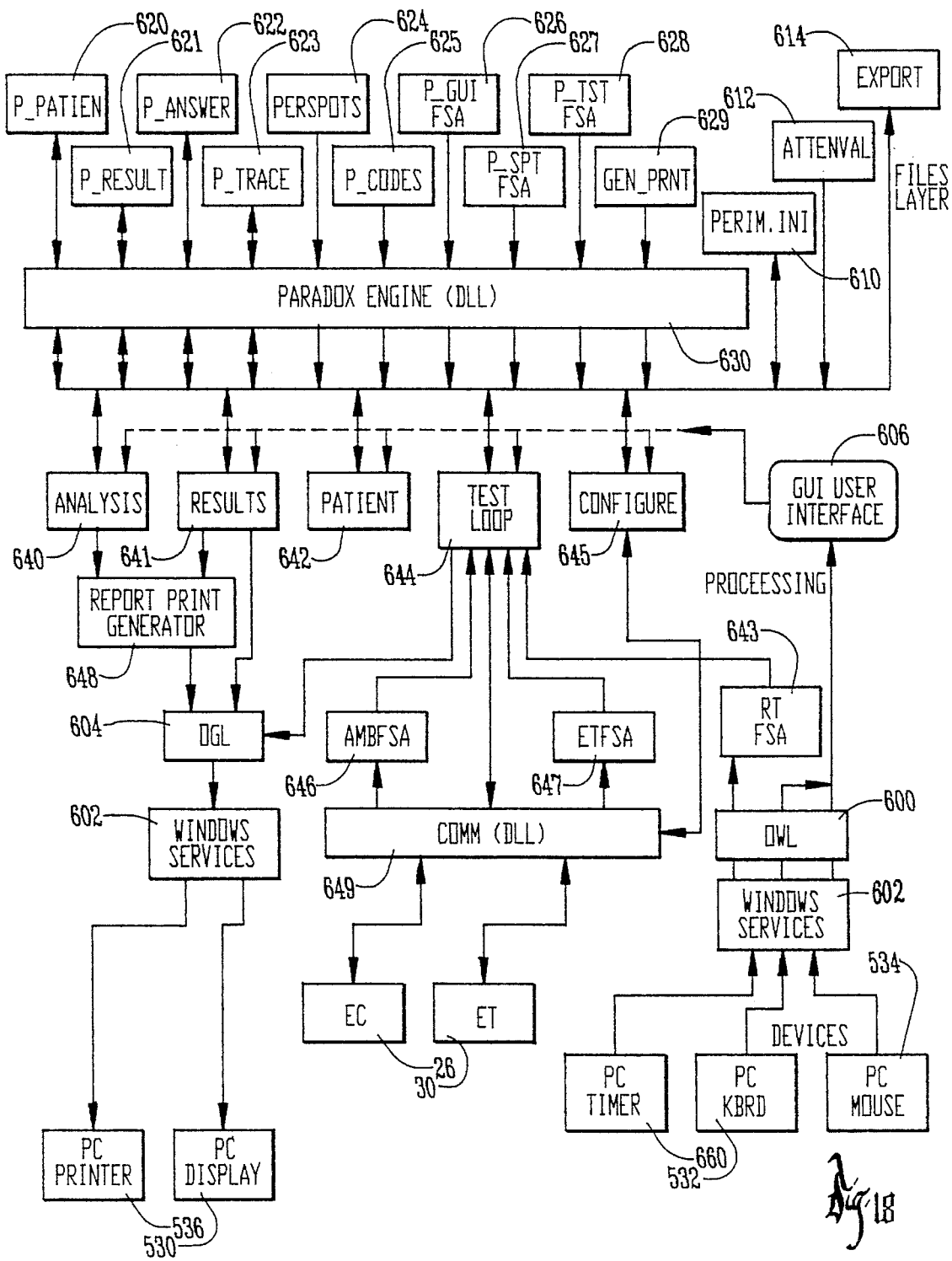
FIG. 18 is a block diagram depicting the software architecture according to the apparatus of the present invention.

Certain software processes are not FSA's. For example:

(1) Main screen generation control:

(1) Displays main menu and enable/disable various menu items;

(2) Displays HOV (hill of vision) in its various formats;

(3) Displays clinician command buttons based on the state of GUIFSA (652, FIG. 20);

(4) Displays eye monitor 542 and updates pupil position and size;

(5) Displays current patient name;

(6) Displays current test type and strategy;

(7) Displays current eye;

(8) Displays current test state (active, ready, testing, etc.);

(9) Displays test statistics (elapsed time, trials, possible errors, etc.);

(10) Intercepts clinician commands and sends them to main GUIFSA (652, FIG. 18).

At initialization this part of the software sets up active flags for buttons, prompts, text, others, and menu items for all the states of main GUIFSA 652. During execution, it will be called by other FSA's or modules to display objects on the main screen. For each type of object (HOV, EM (eye monitoring display 542), button, prompt, text, menu) it contains a method for displaying that object class. The associated method calls upon methods in OGL 604 to paint the objects on screen 530. The exception is the EM method. This method does its own painting on screen 530 (not via OGL 604)

(2) Report printing generator (648 and 629, FIG. 18):

(1) Generates the report requested by the user (the report contents are defined in a Paradox table). It also sends the report to requested designation.

e. Main Data Files and Their Function

The present invention utilizes ASCII files and data bases, stored as Paradox tables. The Borland Paradox Engine is used to access the data in these tables. Some data bases utilize other structures. FIG. 18 illustrates these files and data bases at reference numerals 610–629. The following chart identifies the contents of each file and data base (some of which contain FSA's):

(1) P_patien.db—Stores the patient particulars and latest prescription for both eyes as a Paradox Table 620.

(2) P_result.db—Stores as Paradox Table 621 the results of all static test types for all patients. This table is designed so that different test types can be stored. It is referenced to the P_patien.db by an index. The HOV values are not stored here.

(3) P_answer.db—Contains the other part of the result file as Paradox Table 622. It stores the values of the spots contained in the HOV's, and contains the spot values of all the results of all the static tests for all the patients. It is also referenced to the P_patien.db and the P_result.db by indices.

(4) P_trace.db—Contains in Paradox Table 623 parameters of patient behavior during the test run. It can be used to analyze more closely how the patient responded to each stimulus and what the patient's fixation was during a stimulus. It is a useful as a research tool for future developments. Specifically, it is a record of every stimuli given, the order in which they were given, the response of the patient, the pupil position, a time stamp and some other test parameters.

(5) P_guifsa.db—contains main GUIFSA 652 and controls the main screen clinician interface.

(6) Perspots.db—a Paradox Table 624 which contains the definition of all the spots to be tested for each static test type. For each spot it contains the position, the expected value, the children to be spawned by this spot and the short term fluctuation coefficient. There are also 12 fields for the spot's neighboring spots.

(7) P_sptfsa.db—a Paradox Table 627 which contains the FSA used in testing each type of spot on the HOV. It holds all the strategies for all test types.

(8) P_tstfsa.db—Holds all the FSA's which control the progression of a test run. It holds in Paradox Table 628 the FSA's for all static tests.

(9) P_codes.db—Defines the mapping of test and strategy types to test flow FSA's indices. It also contains the test names and whether the tests are central, peripheral or full field, as well as containing the test category (screening, thresholding, custom, auto diagnostic, etc.) in Paradox Table 625.

(10) Gen_prnt.db—Reports printed by the perimeter are generated using this Paradox Table 629. It contains the design for each report type in a list of fields to be included, their position on the report, their full name and size, and any function which needs to be run to calculate the values of the fields.

(11) Perim.ini—(Perimeter Windows Ini file)—An ASCII file 610 in the Windows 'Ini' file format, defines the starting parameters for the system.

(12) Attenval.dat (NDF attenuation matrix)—An ASCII file 612 containing the neutral density filter (NDF) attenuation factors for the NDF in the engine controller 26.

(13) P_patien.db, P_result.db, P_answer.db and P_trace.db—A P_patient record index is contained in each P_result record which contains a test result for that patient. A P_patient record index and P_result record index is contained in each P_answer record which contains spots for that result of that patient. A P_patient record index and P_result record index is contained in each P_trace record which contains trace data for that result of that patient.

f. Software Communications

Communication between the software and engine controller 26 and eye tracker 30 is accomplished with both software in PC 48 and firmware in EC 26 and ET 30.

Communications Dynamic Link Library (DLL) 649 is a collection of subroutines (not objects) which is available to all programs running on PC 48. It is not a part of the perimeter code proper. These subroutines allow the perimeter program (or any other program) to communicate with a peripheral device via the RS232 port(s). DLL 649 provides all the low level and high level services for communicating with engine controller 26 and eye tracker 30 via the RS232 link.

FIG. 20 is a block diagram of the internal interfaces developed for the software (and not showing standard Windows interfaces) relative to communication between these hardware and software components. Communication exists on a single RS232 line running at 14.4K baud. PC 48 is always the master and initiates all the communications. Using the reset (RTS) line of PC 48, the PC selects the external device with which it is to communicate. It can then either hardware reset the selected device or communicate with it using a protocol which is common to both EC 26 and ET 30.

g. Software Cooperation

All of the pieces described above with respect to FIG. 18 work together to control the operation of the perimeter. In a classical programming approach, one would have a large "main" program which would execute the various parts of perimeter functions; calling subroutines as necessary. In the event driven OOP approach, code objects are sent messages by Windows or other code objects via Windows. The messages cause these objects to be invoked (executed) by Windows. Upon invocation, the object examines the content of the message and performs the appropriate action.

Messages can be generated by the operator via Windows. For example, if the operator points the mouse to the results menu and clicks, then the Results object 641 (FIG. 18) will be invoked when Windows informs it of the mouse action.

During the running of a test, the test sequencing is clocked by PC timer 660. Every 50 ms a message is sent to RT FSA object 643 which causes its execution. This is similar to clocking a hardware state machine. The timer FSA object 643 then decides what, if anything needs to be done during that time increment (e.g. poll ET 30 for pupil information).

h. Main Screen and Menus

Below is a discussion of the information and displays that operate with the software according to the apparatus of the invention. By referring to FIG. 21, it can be seen that the main screen on display 530 contains essentially three separate parts. The main portion, comprising a majority of the screen, is a visual representation of the interior of dome 20 and corresponds with the patient's vision field. It is represented as a Cartesian (X-Y) grid with units of degrees. This grid can be mapped by a mathematical transformation onto the surface of the dome and hence to the corresponding points on the patient's retina. The points which will be tested for the current test type and strategy are shown with an asterisk. In the terminology of the apparatus of the present invention, this is a visual representation of what will be called the "hill-of-vision" of the patient, such as is known in the art.

The second portion of the screen is shown in the lower left hand corner of FIG. 21. It consists of the eye monitor 542 (EM 542)—and is a representation of the video data from eye tracker 30, showing the patient's pupil position and size. This information is dynamically displayed during the testing.

The third portion of the screen contains conventional information for the operator such as the main menu (across the top of the screen), test definition and status data(upper left hand corner—including test type, test strategy, eye under test, and current state or activity of the perimeter), control buttons 546 (upper right hand portion of screen), and test status data (bottom right hand portion—including elapsed time and other test performance parameters).

The main menu allows display and operator interaction regarding the various operational modes of the apparatus. For example, under the "patient" portion of the main menu, another screen (or "window") would come up onto the display and allow editing of information regarding identification of the patient (including patient refraction prescription, lenses to be used in the testing, patient name, etc.) to be entered via keyboard 532. Software also allows a list of patients to be built up and stored, along with records of each test result. This information can then be retrieved and utilized.

The "test" portion of the main menu allows the operator to select such things as type of test and test pattern. Test type can include threshold testing, screening testing, automatic diagnostic testing, and kinetic testing; all as are known in the art. Likewise, a variety of different patterns, including central, peripheral, special, and customized patterns can be selected.

During most of the testing, what will be called parameters can be selected by the operator and changed as desired. Examples are: threshold strategy (e.g. full, full from prior data, fast), fixation target (e.g. central LED, small diamond LEDs, large diamond LEDs), blind spot check size, stimulus size, test speed, and spot duration (e.g. 200 ms, 300 ms).

The "results" portion of the main menu relates to the ability of the operator to select from the data stored on the computer's hard disk a patient and one of the patient's results to be viewed and/or printed.

The system also allows different types of displays to be selected. For example, FIG. 22 shows a conventional hill of vision display. The results of the test run are shown for a particular patient, indicating correct responses, errors, and fixation losses. Type of testing, elapsed time and trials are also illustrated for the operator.

Alternative display types include profile displays, which presents a cross-section of the hill of vision of FIG. 22 and a gray scale display, which shows less sensitive areas of the retina as darker regions. Other display types are possible.

The software also allows such options as a "print type" display which allows the operator to select the type of display to be printed out. An "export test" selection allows any test results to be exported to an ASCII file. The results are then accessible for further analysis by external tools such as statistical analysis software, for example. The software also allows the operator to choose help from the main menu to provide assistance information.

i. Program Execution Examples
ENTER PATIENT DATA

Following are specific examples of how the software according to the present invention operates. Upon invocation of the perimeter program, the program initializes the EC 26 and ET 30 hardware and presents the main screen and menu to the operator.

The operator then prepares to run a test by entering (or retrieving) patient information. The operator clicks the Patient menu item (see FIG. 21) (with mouse 534) and the Patient object (642, FIG. 18) is invoked and (among others) the following things happen:

1. The Patient Information window appears on the screen as commanded via OWL 600, OGL 604 and Window 602.
2. Within the patient screen, a list of existing patients (and their results) is shown. The Patient object 620 gets this data by calling the Paradox Engine DLL 630 to access the appropriate tables.

The operator then enters (or selects) the patient and clicks the OK button in the patient menu and the following happens:

1. If the patient data is new or was updated, the new data is written to a appropriate table via the Paradox Engine DLL 630.
2. The Patient Information window disappears.
3. The selected patient is now the active patient and his/her name appears on the main screen.

Other menu selections operate similarly.
PERIMETER TEST

The actual visual field test (testing the patient) is the most complex operation performed by the perimeter software. The software must coordinate several processes which are simultaneously active, including:

1. Moving the EC motors (180, 182, 184, 188, 192) to position the stimulus.
2. Presenting the stimulus (open and close EC shutter 146 via shutter motor 412).
3. Monitoring the patient response (patient switch 40 on EC 16).
4. Monitoring/controlling the ambient light in bowl 20 (via EC background lamp driver 416 and sensor 408).
5. Monitoring/controlling the spot brightness (via EC projector lamp driver 414 and sensor 406).
6. Monitoring the patient's pupil size and position as determined by ET 30.
7. Updating display 530 as the test progresses.
8. Responding to operator requests (e.g. pause).

The tasks are coordinated by the Timer FSA object 643 using a time line (FSA) as shown in FIG. 19 (for one stimulus presentation). Every 50 ms the Timer RTFSA, object 643, is invoked by a message sent by Windows. The Timer FSA object 643 examines its location within the time line to determine what action should be taken. First the stimulus is presented, then the motors are moved for the next stimulus. Concurrently (task-wise, not real-time-wise), ET 30 is being polled periodically for pupil information and is waiting for the patient to respond to the stimulus. When ET data is received, the pupil size and position are updated in eye monitor window 542 on screen 530. When the patient responds, the hill-of-vision on the screen is updated. When the test has completed the results are automatically written to a table (database) via the Paradox Engine DLL 630 and the Testloop object 644 is no longer invoked. The system then becomes static and waits for further operator input.

The foregoing presents a high level summary of the perimeter software and firmware. Specific implementation in software and firmware are within the skill of those skilled in the art.

K. Alternatives to the Apparatus

It is submitted that one skilled in the art will be able to clearly understand the apparatus sufficiently to make and use the invention with this information.

It will be appreciated that the present invention can take many forms and embodiments. The true essence and spirit of the invention are defined in the appended claims, and it is not intended that the embodiment of the invention presented herein should limit the scope thereof.

We claim:

1. An automated perimeter comprising:

a base;

a patient interface connected to the base and spatially adjustable to the patient's head and eyes;

a dome associated with the patient interface and adjustably moveable between a first position adjacent the patient interface and a second position away from the patient interface.

2. The perimeter of claim 1 further comprising a projector including a visual stimulus placeable at various locations on the dome.

3. The perimeter of claim 2 further comprising a housing connectable to the dome including the projector, the dome including an aperture through which the projector presents the visual stimulus.

4. The perimeter of claim 2 further comprising a connector to electrically connect the perimeter to a controller.

5. The perimeter of claim 2 wherein the projector includes a light source, optics, beam size controlling means, a shuttering means and focusing means.

6. The perimeter of claim 1 further comprising an eye sensor including a detector of size and position of a pupil of a patient's eye being tested.

7. The perimeter of claim 6 wherein the eye sensor includes a housing which contains all parts of the eye sensor, the dome including a second aperture through which the eye sensor can view the patient's pupil.

8. The perimeter of claim 6 further comprising a connector for electrical connection to a controller.

9. The perimeter of claim 6 wherein the eye sensor includes an imager for capturing and digitizing an image of the patient's eye.

10. The perimeter of claim 1 further comprising a patient interface including a manually actuatable switch.

11. The perimeter of claim 10 wherein the patient interface includes a connector to connect the switch to the perimeter.

12. The perimeter of claim 1 further comprising a controller including a processor and a connector to electrically connect the processor to the perimeter.

13. The perimeter of claim 1 wherein the base has a size which is generally portable.

14. The perimeter of claim 13 wherein the base is moveable on a floor surface.

15. The perimeter of claim 13 wherein the base is moveable on a table surface.

16. The perimeter of claim 13 wherein the base is releasably connectable to a pole by a connection device.

17. The perimeter of claim 1 wherein the dome is approximately 60 centimeters in diameter.

18. An automated perimeter comprising.:

a base;

a patient interface connected to the base and spatially adjustable to the patient's head and eyes;

a dome associated with the patient interface and adjustably moveable between a first position adjacent the patient interface and a second position away from the patient interface;

an interior hemispherical surface on the dome upon which a visual stimulus can be placed;

a first modular housing containing a visual stimulus generating and projection device to project the visual stimulus through a first opening in the dome to a selected but adjustable location on the interior hemispherical surface of the dome;

a second modular housing removeably attachable to the dome at or near a second opening in the dome;

the second modular housing containing an eye sensing devise to sense the position and diameter of a patient's pupil through the second opening; and releasable electrical connections between the first and second modular housing and an electrical communications path to a stand alone processor device.

19. The perimeter of claim 18 wherein the first and second housings are substantially smaller than the dome.

20. The perimeter of claim 18 wherein the first modular housing includes a light source, one or more devices to create a point light source, and a device to divert the point light source to an adjustable direction device extending through the first opening to direct a visual stimulus to various locations over a substantial portion of the surface of the dome.

21. The perimeter of claim 20 wherein the adjustable direction device includes an azimuthal pointing member and an elevational pointing member.

22. The perimeter of claim 20 further comprising a device to equalize distance between the light source and the location of the point light source on the surface of the dome.

23. The perimeter of claim 20 further comprising a device to vary the intensity of the light source.

24. The perimeter of claim 20 further comprising a device to vary the size of the point light source.

25. The perimeter of claim 20 further comprising a device to vary background illumination of the dome.

26. The perimeter of claim 20 further comprising a device to vary the duration of the light source.

27. The perimeter of claim 26 further comprising a visually perceivable fixation device.

28. The perimeter of claim 18 wherein the second modular housing includes an image receptor, and an image processing circuit.

29. The perimeter of claim 28 wherein the fixation device comprises a light source in a third opening in the dome.

30. The perimeter of claim 28 including light sources to illuminate a patient's pupil.

31. An automated perimeter comprising:

a base;

a patient interface connected to the base and spatially adjustable to the patient's head and eyes;

a dome associated with the patient interface and adjustably moveable between a first position adjacent the patient interface and a second position away from the patient interface;

an imaging device having means for continuously capturing an image of a patient's eye; and an image processing circuit connected to the imaging device having means for identifying and locating the eye and continuously monitoring the size and position of the eye.

32. The device of claim 31 wherein the imaging device is a CCD imager.

33. The device of claim 31 wherein the image processing circuit includes a device to locate and recognize an image as a pupil of an eye.

* * * * *